(12) United States Patent
Weber

(10) Patent No.: US 6,454,743 B1
(45) Date of Patent: Sep. 24, 2002

(54) INJECTION DEVICE

(75) Inventor: Wilfried Weber, Schopfloch (DE)

(73) Assignee: Schering Aktiengesellschaft, Berlin (DE)

(*) Notice: Subject to any disclaimer, the term of this patent is extended or adjusted under 35 U.S.C. 154(b) by 0 days.

(21) Appl. No.: 09/674,253

(22) PCT Filed: Apr. 24, 1999

(86) PCT No.: PCT/DE99/01244
§ 371 (c)(1),
(2), (4) Date: Oct. 30, 2000

(87) PCT Pub. No.: WO99/56805
PCT Pub. Date: Nov. 11, 1999

(30) Foreign Application Priority Data

Apr. 30, 1998 (DE) .......................... 198 19 409

(51) Int. Cl.[7] .............................. A61M 37/00
(52) U.S. Cl. .................. 604/131; 604/135; 604/232
(58) Field of Search ................. 604/131, 134, 604/135, 136, 157, 152, 232; 600/583

(56) References Cited

U.S. PATENT DOCUMENTS

| | | | | |
|---|---|---|---|---|
| 4,445,510 A | * | 5/1984 | Rigby | 604/136 |
| 5,026,349 A | | 6/1991 | Schmitz et al. | |
| 5,092,842 A | * | 1/1992 | Bechtold et al. | 604/135 |
| 5,137,516 A | | 8/1992 | Rand et al. | |
| 5,383,865 A | * | 1/1995 | Michel | 604/232 |
| 5,478,316 A | * | 12/1995 | Bitdinger et al. | 604/135 |
| 5,480,387 A | * | 1/1996 | Gabriel et al. | 604/134 |
| 5,514,097 A | * | 5/1996 | Knauer | 604/136 |
| 5,843,036 A | * | 12/1998 | Olive et al. | 604/136 |
| 5,876,378 A | * | 3/1999 | Mbadugha | 604/152 |
| 6,015,392 A | * | 1/2000 | Douglas et al. | 600/583 |
| 6,099,503 A | * | 8/2000 | Stradella | 604/135 |

FOREIGN PATENT DOCUMENTS

| | | | |
|---|---|---|---|
| DE | 31 13 977 | 11/1982 | |
| DE | 89 12 091 | 1/1990 | |
| DE | 37 15 340 | 10/1995 | |
| FR | 2 567 760 | 1/1986 | |
| FR | 2 733 155 | 10/1996 | |
| HU | WO88/00843 | * 2/1988 | ............ A61M/5/20 |

* cited by examiner

Primary Examiner—Teresa Walberg
Assistant Examiner—Leonid Fastovsky
(74) Attorney, Agent, or Firm—Browdy and Neimark

(57) ABSTRACT

An injection device that is used with a syringe, wherein the injection needle of the syringe is initially introduced into the skin and the injection fluid is injected afterwards. The injection device is essentially driven and controlled by a control sleeve (6) which can be displaced and/or rotated in relation to the housing (7) and which can be moved between a closing and functional position (P1) and an open and safety position (P2). In the closing and functional position, the control sleeve prevents access to the syringe and activates a release device for the injection process. In the open and safety position, a syringe (1) can be removed or inserted. A plurality of components carrying out the injection process (a slide (2) in which the syringe (1) is placed and a plunger (4) that impinges upon the syringe piston) are moved or controlled depending on the movement and position of the control sleeve or supported (for example, an ejection device for the syringe or a signaling device informing that injection has been completed). The device enables full-automatic injection that can be reliably carried out by patients themselves with few handling procedures.

48 Claims, 19 Drawing Sheets

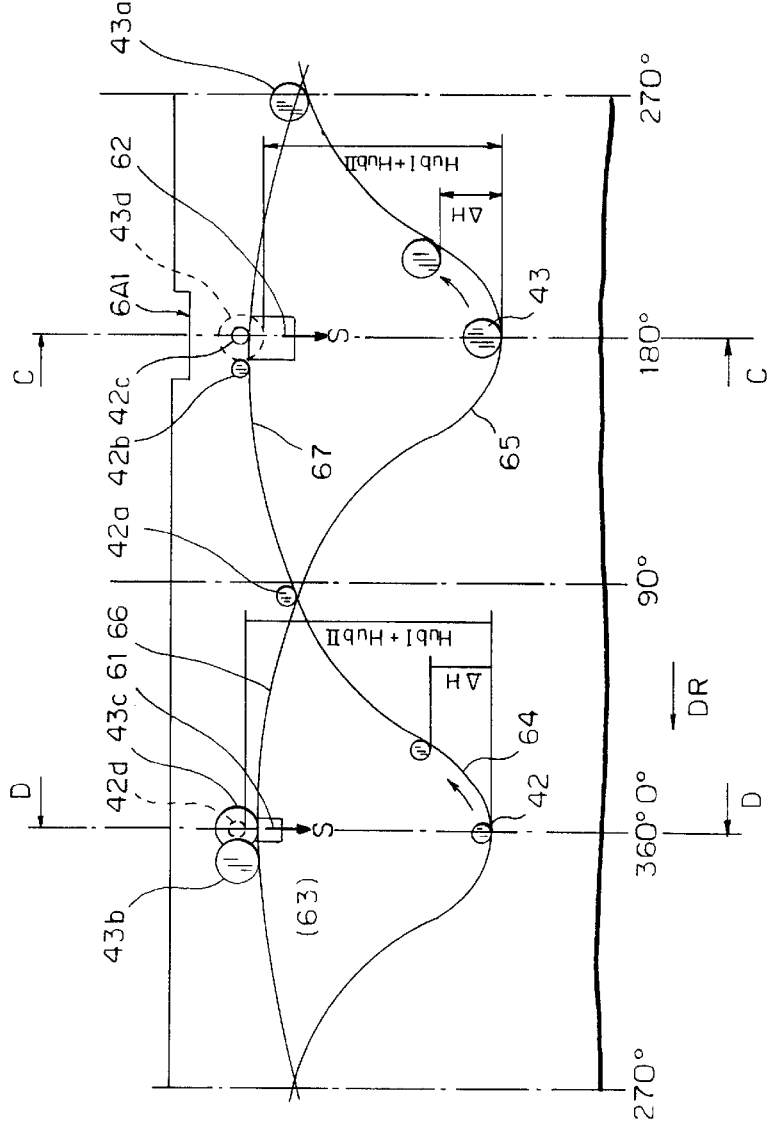

FIG. 15A
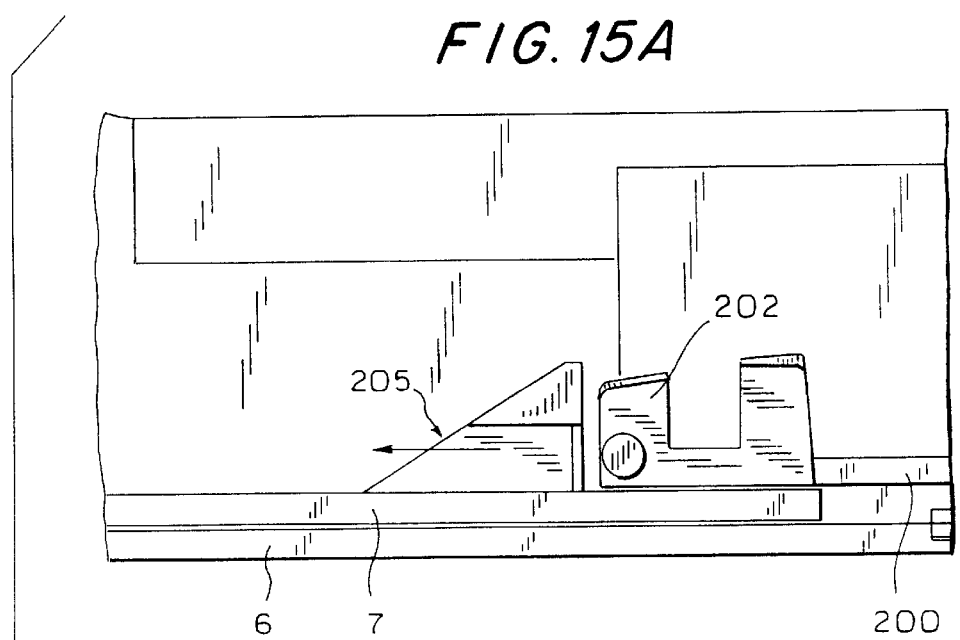
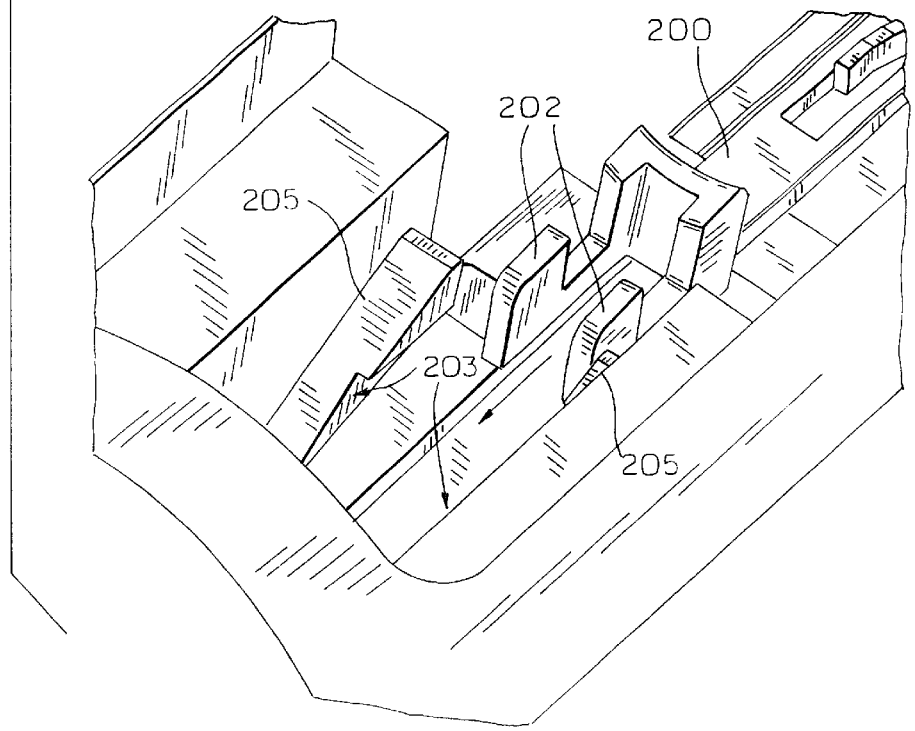

FIG. 15B
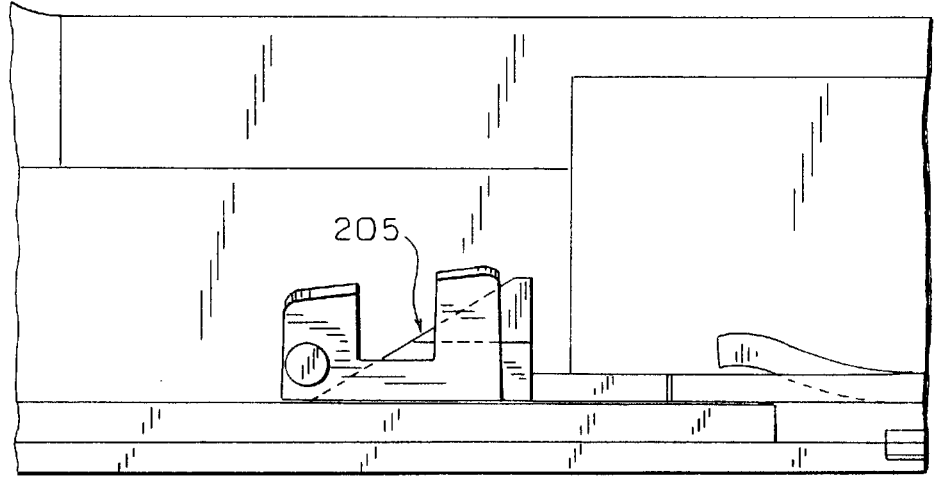
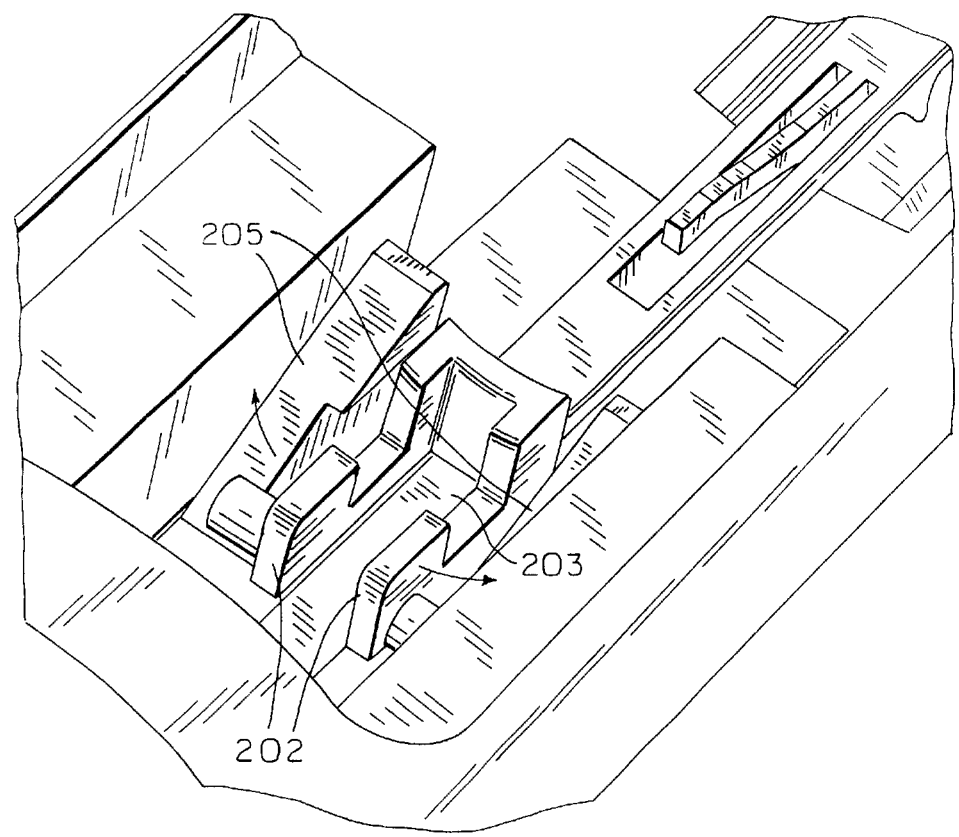

INJECTION DEVICE

CROSS REFERENCE TO RELATED APPLICATION

The present application is the national stage under 35 U.S.C. 371 of PCT/DE99/01244, filed Apr. 24, 1999.

TECHNICAL FIELD OF THE INVENTION

The invention relates to an injection device with a syringe, in particular a disposable syringe, for injecting an injection fluid under the skin.

Carrying out medically appropriate injections by means of a syringe presupposes a minimum degree of medical knowledge and practical skill. Adherence to these requirements is usually guaranteed in the stationary hospital or care sector, since, here, syringes are handled by medically trained specialized personnel; however, with the increase in chronic illnesses due to the increasing life expectancy of the population, the domestic care sector is also increasing.

The result of this is that the handling of syringes must increasingly be capable of being carried out by the medical lay public as patients for the purpose of self-treatment at home; apart from a certain threshold of inhibition when a syringe is applied, adherence to the above-mentioned criteria is also no longer guaranteed as the age of the patient increases, for example because of motor disturbances or impaired vision. This has increasingly led, in recent decades, to the design of injection devices which operate partially or completely automatically and into which, in particular, conventional ready-made syringes can be inserted, so that it only remains for the patient to position the front end of this injection device on the place of injection and then actuate a trigger means in the injection device, in particular by finger pressure, whereupon the pricking of the needle and the injection of the injection fluid are then carried out mostly under the effect of a spring means. Examples of such injection devices are shown in DE 29 50 140 C2, DE 14 91 842 C2, DE 24 36 000 C2, EP 0, 144,625 B1, EP 0, 516,473 B1 and EP 0, 577,448 A1.

PRIOR ART

The invention proceeds from a generic device, such as is described by FR 2 733 155 A. This injection device contains built-in parts which are held in the housing and which, under the action of a spring as drive means, load the syringe in such a way that, as a result of a successive linear displacement of the syringe and of the injection needle in the housing, first the introduction of the injection needle of the syringe under the skin takes place and only thereafter is the injection fluid injected. After injection has taken place, these structural parts are then returned to their initial position again as a result of an opposite movement. Within this cycle of movement, it is necessary to extract the emptied disposable syringe from the injection device and replace it by a filled, new disposable syringe, so that the injection operation can then be restarted anew.

To that end, the housing has an axially displaceable control sleeve, which after the return of the built-in parts that effect the linear displacement is drawn into an opening position, whereupon a new disposable syringe can be put in place and the control sleeve can be thrust into a closing and operating position. The tension of the spring that effects the injection stroke is generated here upon retraction of the control sleeve, until a locking position is reached, to which end the spring force to be overcome must be fully brought to bear by the patient to its full extent as a tensile or compressive force. The execution of one complete injection cycle in this design requires a plurality of a successive handling actions in a fixed order.

U.S. Pat. No. 5,137,516 A shows an actuation unit and a housing unit for receiving the syringe, which for actuating the syringe must be placed against one another in axially aligned fashion and joined together. To that end, a screw sleeve is provided which is a component of the housing unit, and onto which the actuation unit can be screwed once a filled syringe has been put in place, and from which the actuation unit has to be unscrewed again after the injection has been made, so that the empty syringe can be removed.

German Utility Model DE 89 12 091 U shows an injection device operating in a single stage, in which the piercing of the skin and the injection proceed simultaneously. As in the aforementioned U.S. Pat. No. 5,137,516, an actuation unit and a housing unit for receiving the syringe are provided, but they are disposed fixedly parallel to one another and thus form a structural unit. A "column" is axially guided in the actuating unit and has a plate on its upper end that by rotation of the column either blocks or releases the insertion opening of the housing unit, thus defining a closing and operating position and an opening position relative to the housing unit.

The handling of both these last two injection devices when the disposable syringe is being changed requires, particularly when the two housing parts, together with the reinserted, new ready-made syringe, are brought together accurately in terms of fit and direction, some degree of manual skill which cannot be presupposed in the group, referred to above, of chronically sick, older people; this previously known solution is therefore somewhat unsuitable for this group in particular.

SUBJECT OF THE INVENTION

The essential object of the invention is to develop generic injection devices in such a way that, whilst having a simple mechanical design, the patient's actions required for handling are reduced to a minimum, in particular the extraction and insertion of the disposable syringe are simplified to such an extent that only minimal requirements are demanded of the (remaining) physical and mental abilities of the patient.

This object is achieved, according to the invention, in conformity with the defining part of patent claim 1.

The essential idea of the solution according to the invention is to combine a multiplicity of drive, control and safety functions in a central structural part, the control sleeve, which manually is extremely easy to handle, since it needs merely to be rotated relative to the housing:

The control sleeve is part of the housing inasmuch as it serves, instead of, for example, a flap, for closing and for opening the interior of the housing, in which the ready-made syringe is held.

The control sleeve is part of the drive means insofar as, when the housing is being opened by the rotation of the control sleeve, a counterstroke of the slide and tappet is generated counter to the action of a spring executing the injection strokes, said counterstroke conveying these two structural parts into their original locking position again, separate measures and actions not being required for this absolutely necessary sequence.

The control sleeve is also a control means insofar as, depending on its position, it blocks the trigger means of the injection device or permits its activation.

The control sleeve also makes it possible to have further advantageous embodiments of the solution according to the invention for increasing the operating safety and handling convenience, insofar as it directly actuates an ejection means which, after injection has taken place, automatically presses the empty ready-made syringe toward the patient, when the housing is opened, by means of the control sleeve, and thus makes extraction easier, and said control sleeve is also utilized for feedback of the position and operating state of the injection device, said feedback being capable of being easily detected by the patient's senses.

Other advantageous embodiments according to the invention relate to a clearly detectable, acoustic signal means, by which the end of an injection operation is indicated to the patient.

This diversity of functions can be implemented by means of a simple design of the injection device; thus, the essential structural parts of the injection device can, for example, take the form of injection moldings which can easily be mounted, so that the injection device can be produced cost-effectively in terms of material and labor.

BRIEF DESCRIPTION OF THE DRAWINGS

Preferred exemplary embodiments of the injection device according to the invention are now explained in more detail by means of the drawings in which:

FIG. 13 is a developed view of the inner casing surface of the control sleeve in a variant having two control cams, FIGS. 14A, B are sections taken in the planes C—C and D—D through the casing part of the control sleeve of FIG. 13, FIGS. 15A, B, C shows sections and perspective views of the ejection means, FIGS. 16A, B, C, D shows perspective views of one exemplary embodiment of the slide with an integrated gear, FIGS. 17A, B, C shows views and a longitudinal section through the gear side of FIG. 16.

DESCRIPTION OF THE PREFERRED EXEMPLARY EMBODIMENT

Figure 1:
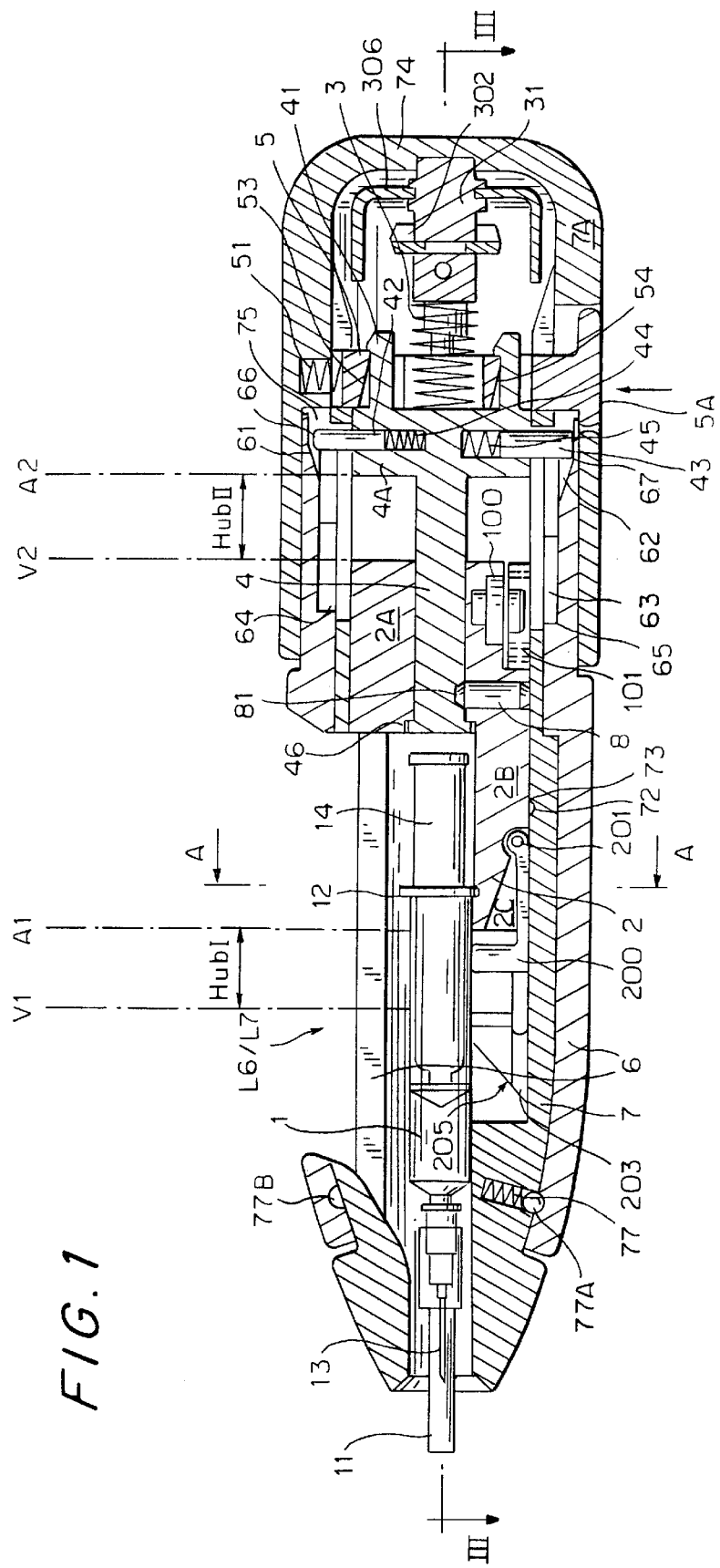
FIG. 1 shows a first longitudinal section through the injection device in its opening position for the insertion or extraction of the syringe, in the plane I—I of FIG. 3.

The basic design of the injection device according to the invention will be explained first, followed by the individual operating segments within a work cycle.

The injection device possesses, as it were as a "mechanical supporting skeleton", a housing 7, the front portion 7C of which tapers conically where the needle 13 of the syringe 1 emerges, said housing being designed essentially cylindrically in its middle portion 7B and merging into a rear, caplike handling portion 7A with a housing rear wall 74 having an annular groove 75. The longitudinal axis F of this housing 7 forms the longitudinal axis, that is to say that axis 30 in which the syringe 1 is held and in which the essential movements and control operations for injection also consequently take place.

The housing 7 has, in its middle portion 7B adjoining the front portion 7C, a loading orifice L7 which extends over an acute circumferential angle with respect to the longitudinal axis F, in the exemplary embodiment illustrated, the middle part of the housing 7 extending over an angle α2 of about 270°, so that the loading orifice L7 of the housing 7 occupies approximately a circumferential range of 90°. The interior of the housing 7 is accessible via this loading orifice L7 for the insertion and extraction of a syringe 1.

Figure 3:
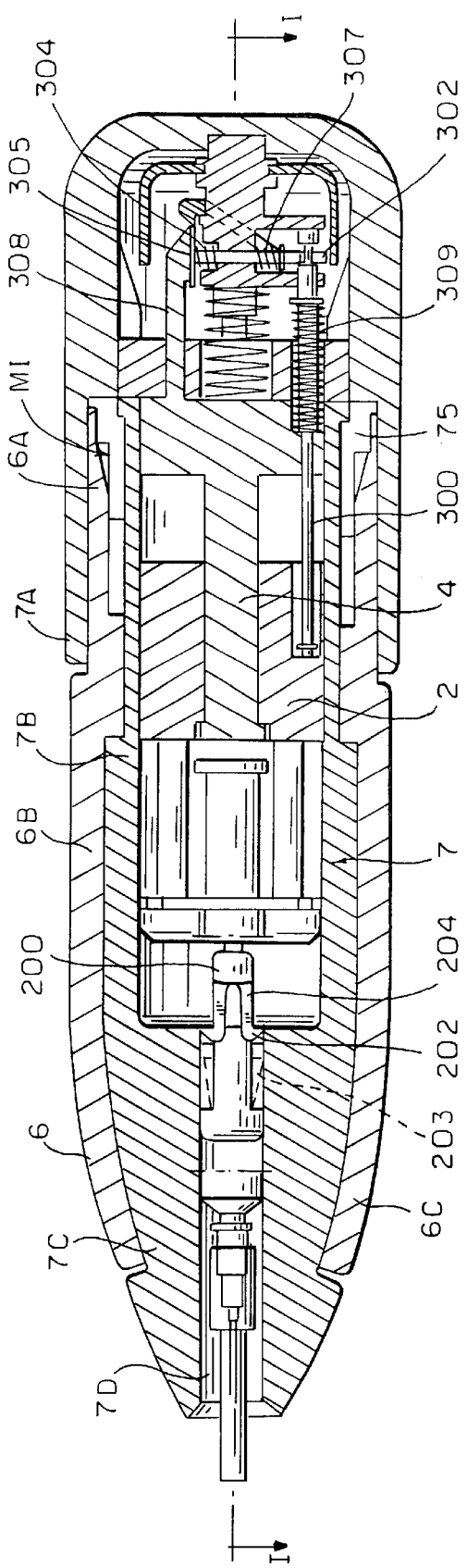
FIG. 3 shows a second longitudinal section through the injection device in its opening position, in the sectional plane III—III of FIG. 1.

In order to make the basic design of the housing 7 clear, the latter is illustrated by close hatching in FIG. 3.

Figure 2:
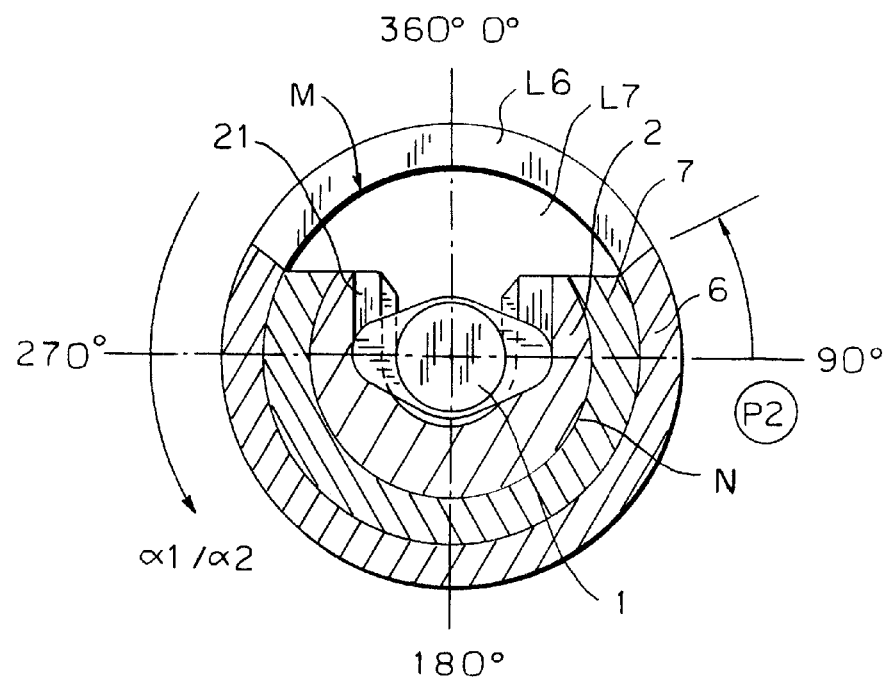
FIG. 2 shows a first cross section through the injection device in its opening position, in the sectional plane A—A of FIG. 1.
Figure 9:
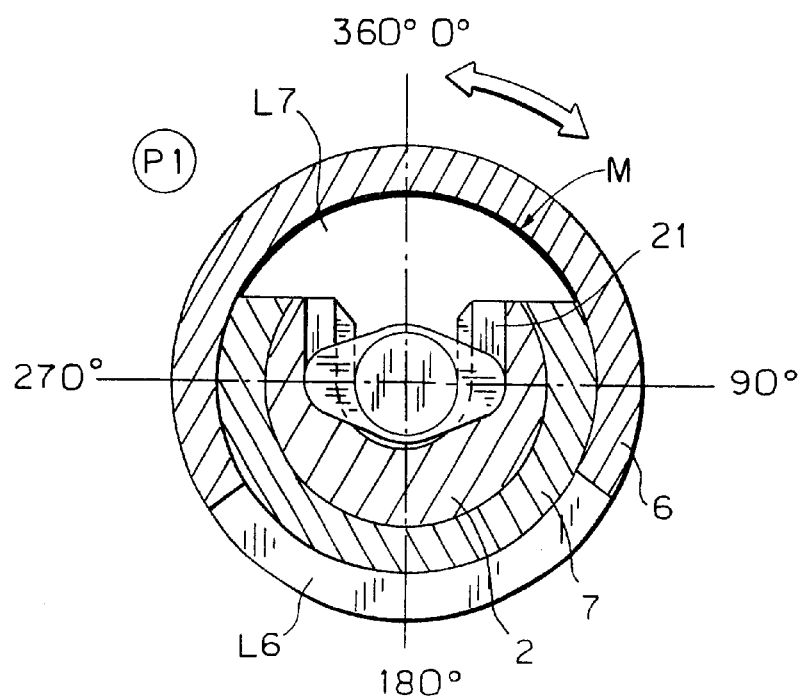
FIG. 9 shows a second cross section through the injection device at the end of the second stroke, in the plane B—B of FIG. 8.

Held on and in this housing 7 is a control sleeve 6 which is a structural operating part particularly essential to the invention and which is rotatable coaxially to the housing 7 about the longitudinal axis, of the latter, as illustrated, in particular, in FIGS. 2 and 9. The control sleeve 6 has, initially, a front, tapered guide portion 6C which is seated essentially positively on the forward-tapering front portion 7C of the housing 7 and which is held rotatably on this portion of the housing 7. Said guide portion has adjoining it an essentially cylindrical middle portion 6B which, over part of its circumference, has a loading orifice L6 for the insertion and extraction of the syringe 1 from the housing 7. This middle region extends over an angle α1 of likewise about 270° correspondingly to the housing 7, so that an orifice angle of likewise about 90° remains for the loading orifice L6.

In a first function, essential to the invention, of this design of the control sleeve 6 and housing 7, the control sleeve 6 slides on the casing surface M of the housing 7 as a result of the rotation of the control sleeve 6 on the latter, so that, in an opening and securing position P2 (FIG. 2), the two loading orifices L6 of the control sleeve 6, on the one hand, and L7 of the housing 7, on the other hand, are essentially congruent, that is to say, in this opening and securing position P2, the control sleeve 6 opens the loading orifice L7 of the housing, so that the user has access to the syringe 1 held in the longitudinal axis F.

As a result of the rotation of the control sleeve 6 on the casing surface M (symbolized by the double arrow in FIG.

9), a position can be produced, in which the control sleeve 6 completely closes the loading orifice L7 of the housing 7 (FIG. 9) and thus defines a closing and operating position P1 of the injection device according to the invention.

This "changeover function" of the control sleeve 6 between the closing and operating position P1 and the opening and securing position P2 is one of the essential functions of the control sleeve.

Another important task, specifically the drive and control function for the multiplicity of structural operating parts which are arranged in the housing and which are also explained further below, is the cooperation of the rear, cylindrical control portion 6A of the control sleeve 6 having an annular groove 75 of the housing 7. The inner casing surface MI of the cylindrical control portion 6A of the control sleeve 6 is provided with profiles or profile tracks which are designed as control cams 64, 65, 66 and 67, as is illustrated in the developed view of the inner casing surface MI of FIGS. 11 and 12. These control cams cooperate with control elements of further structural parts which are held within the housing 7 and serve for generating two injection strokes and the design of which is described below:

The middle portion 7B of the housing 7 (outer casing surface M) is of hollow-cylindrical design, that is to say it also has an inner casing surface N (FIG. 2). In the interior thereby produced in the middle portion 7B slides a partially cylindrically designed slide 2. This slide 2 has a rear first portion 2A, which is designed as a hollow cylinder, and a front approximately semicylindrical second portion 2B which is likewise guided in the housing 7 and which has a groove-shaped or slitlike retention 21 for positioning the syringe collar 12 of the syringe 1, so that the syringe 1 is thereby fixedly positioned and held in the slide 2 in the direction of the longitudinal axis F, that is to say, in particular, the axial position of the injection needle 13 of the syringe 1 in the longitudinal axis F is unequivocally determined by the position of the syringe collar 12 and, consequently, the axial position of the slide 2 in the housing 7.

The axial movement of the slide 2 in the longitudinal axis F is limited between a locking position Al and an advanced position V1 by suitable abutting and securing means within the housing 7, that is to say, in the advanced position V1, the syringe 1 is located with its injection needle 13 in the position extended out of the tip of the housing 7 and functionally ready for injection, and, in the locking position A1, the slide is located in its rear position, in which the injection needle 13 is retracted within the outlet duct 7D in the front portion 7C of the housing 7.

This axial movement of the slide 2 between the locking position A1 and the advanced position V1 is designated below as the "first stroke" H1 (stroke I in FIG. 1). This stroke thus serves for moving the syringe 1 forward as an entire operating unit, that is to say for pricking the needle 13 to the medically required depth of tissue under the skin when the outlet orifice of the duct 7D sits on the skin.

A tappet 4 designed in the manner of a ram is centrally mounted axially displaceably in the first portion 2A of the slide 2. This tappet 4 is designed, at its end pointing toward the handling portion 7A of the housing 7, as a guide portion 4A which has the same outside diameter as the first portion 2A of the slide 2, so that these two structural parts are axially displaceable in the middle portion 7B of the housing 7.

That end face of the tappet 4 which points toward the front end of the injection device is located directly opposite the end face of the syringe plunger 14, so that an axial displacement of the tappet 4 in the slide 2 (in which the syringe 1 is held fixedly) leads to loading of the syringe plunger 14 and, consequently, to the pushing of the syringe plunger 14 into the syringe 1 and to the emission of the injection fluid through the injection needle 13. The tappet 4, too, is thus axially displaceable between two positions, specifically between a locking position A2 (for example, FIG. 6), in which there is no contact with the syringe plunger 14, and an advanced position V2 (for example, FIG. 8), in which the syringe plunger 20 14 is pushed completely into the syringe 1, insofar as there is provision for this, and the injection fluid has been injected in the desired quantity into the tissue via the injection needle 13.

The movement of the tappet 4 between the locking position A2 and the advanced position V2 is designated below as the "second stroke" H2 (stroke II in FIG. 1).

It should be made clear, once again, that the first stroke H1 of the slide 2 leads to the axial advance of the entire syringe 1 and therefore of the injection needle 13 and, consequently, to the pricking of the injection needle 13, whereas only the second stroke H2, the axial movement of the tappet 9, then leads to loading of the syringe plunger 14 and to the injection of the injection fluid through the (pricked) injection needle 13.

Another essential feature of the solution according to the invention, then, is the control-related implementation of these successive first and second strokes H1, H2 for carrying out a complete pricking and injection sequence:

This purpose is served by a pinlike coupling element 8 which is located between the slide 2 and the tappet 4 and which, during the first stroke H1 of the slide 2,10 couples the latter and the tappet 4 to one another via a first catch element 81 in the tappet 4 and, after the expiry of the first stroke H1, releases the coupling by means of a second catch element 73 in the housing 7, so that the tappet 4 alone can then carry out the second stroke H2.

In the exemplary embodiment illustrated, the coupling element 8 consists of a bolt like pin with conically shaped end faces. In a manner corresponding to this shape of the end faces, the two catch elements consist of depressions 72 and 81 in the tappet 4 and in the housing 7 respectively, said depressions being essentially complementary to these end faces, and, in particular, the corresponding conical slopes in these depressions are important.

In the locking position A2 of the tappet 4, the latter is connected to the slide 2 via the coupling element 8, in that the inward-pointing end face of the latter engages into the depression 81 of the tappet 4, whereas there is no depression on the inner casing surface of the opposite portion of the inner casing of the housing 7. Consequently, the tappet 4 and slide 2 are positively coupled in their movement and consequently jointly execute the first stroke which leads to the pricking of the injection needle 13.

Figure 8:
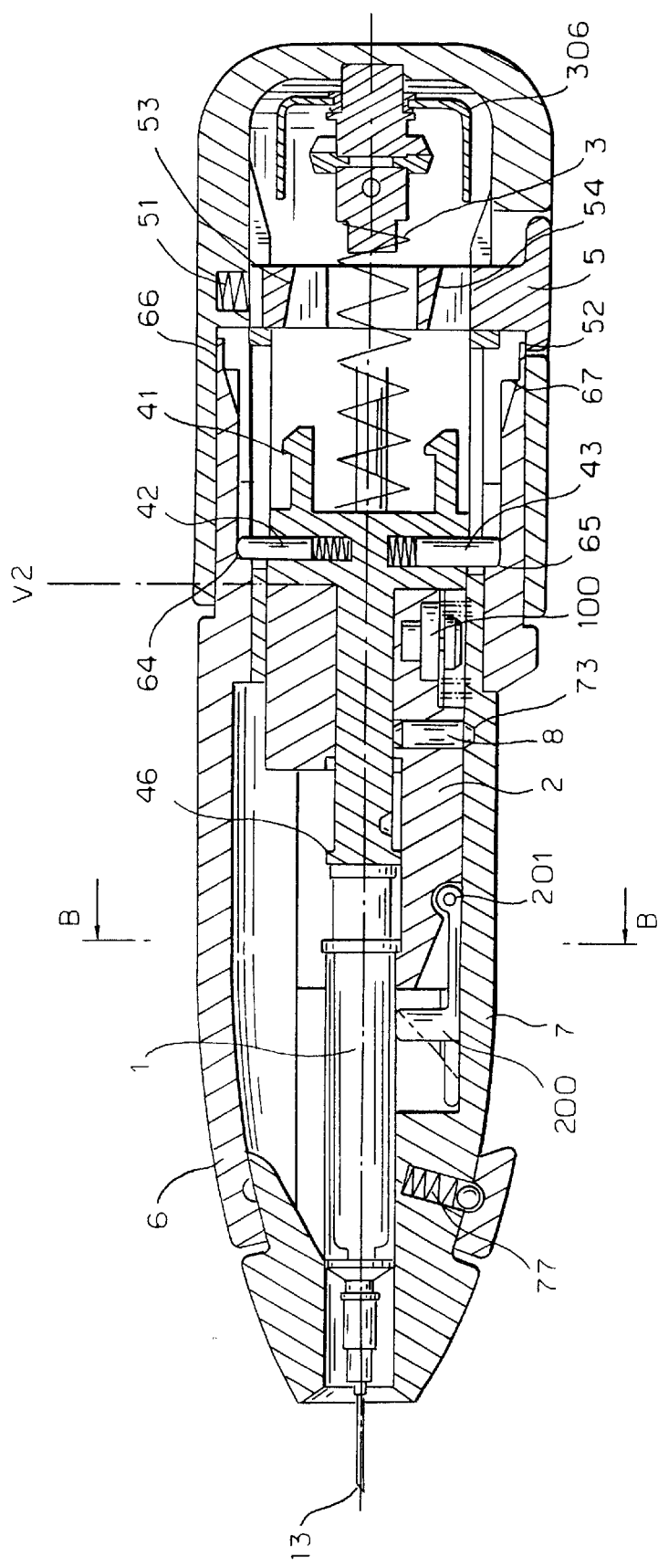
FIG. 8 shows a fifth longitudinal section through the injection device at the end of the second stroke, in the plane of FIG. 1.
Figure 10:
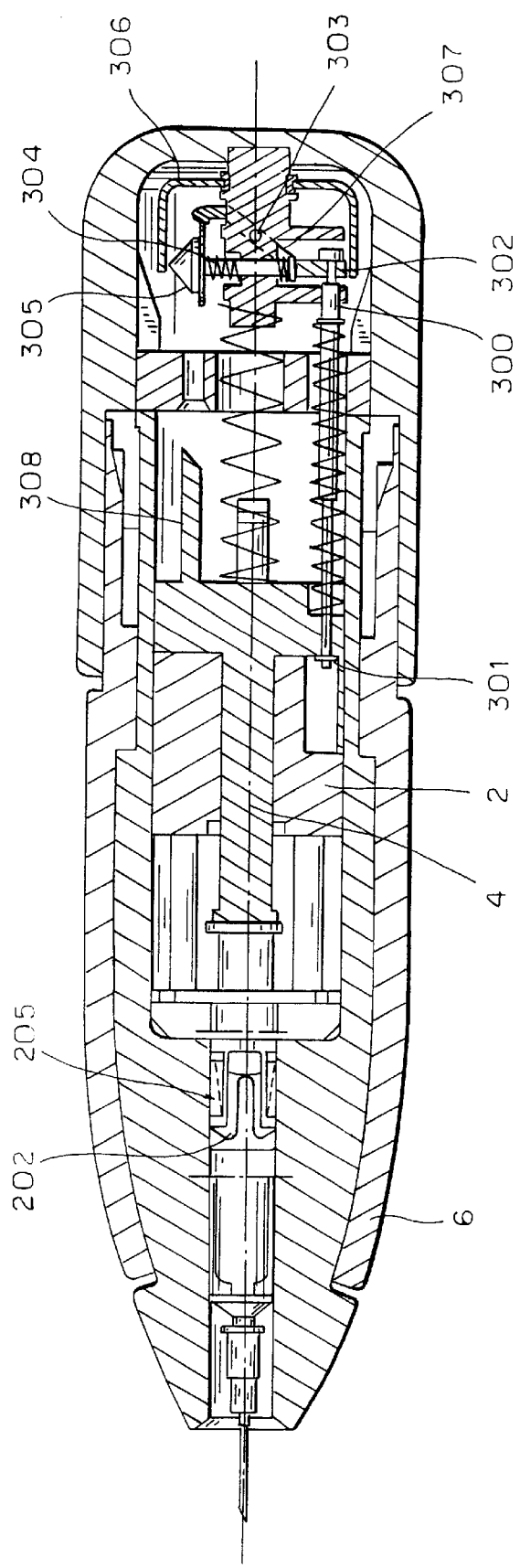
FIG. 10 shows a sixth longitudinal section through the injection device at the end of the second stroke, in the plane X—X of FIG. 8.

The advanced position V1 of the slide 2 is defined correspondingly by the positioning of the depression 72 in the housing 7: as soon as the slide 2 has reached the selected advanced position in the housing 7, the coupling element 8 reaches the depression 72 and, as a result of the conical shape, slides with its end face confronting said depression into the latter, with the result that its opposite end face is freed from the corresponding depression 81 in the tappet 4, the consequence of this being that the positive coupling between the tappet 4 and slide 2 is canceled. Further loading of the tappet 4 in the direction of the syringe 1 then leads, therefore, to the execution of the second stroke H2 for injecting the injection fluid, until the front end face of the guide portion 4A of the tappet 4 rests on the rear end face of the first portion 2A of the slide, thereby defining the advanced position V2 of the tappet 4 (FIGS. 8 and 10).

So that these two strokes H1 and H2 can be carried out in the order described, jointly by the slide and the tappet (stroke 1) and by the tappet alone (stroke 2), a drive means is required, which loads the tappet 4 on its end face pointing towards the housing rear wall 74; for this purpose, in the exemplary embodiment illustrated, a helical spring 3 is provided, which is arranged coaxially to the operational axis F and of which one end is supported on the tappet 4 and the other end is seated on a holding block 31 which, in turn, is held in the housing rear wall 74.

The spring force of this helical spring 3 is dimensioned in such a way that it is sufficient for carrying out the two strokes H1 and H2, that is to say, in particular, up to the complete injection of the injection fluid.

The helical spring 3 is consequently in its tensioned state when the slide 2 and tappet 4 are in their respective locking position A1 and A2.

Between the positions of the tappet 4 and slide 2, on the one hand, and the positions P1 and P2 of the control sleeve 6, on the other hand, a coupling is defined, in that further structural operating parts are provided, which ensure that the slide 2 and tappet 4 must necessarily be in their respective locking position A1, A2 when the control sleeve 6 is in its opening position P2, or, conversely, that only when the control sleeve 6 has assumed its closing and operating position P1 (when the loading orifice L6 closes the loading orifice L7) can the tappet 4 and slide 2 leave their respective locking positions and assume their advanced positions V1 and V2 defined above, being moved by the force of the helical spring 3.

There is provision, furthermore, after injection has been carried out, that is to say when the control sleeve 6 is rotated again from its closing and operating position P1 into its opening and securing position P2, for this rotational movement to ensure, via the profilings, referred to initially, on the casing inside MI, a corresponding return of the tappet 4 and slide 2 into their respective locking positions A1 and A2, in other words access into the housing 7 through the loading orifices L6, L7 can take place only when it is ensured that the tappet 4 and slide 2 are located again in their respective locking positions, in which, of course, the spring 3 is then tensioned again and is ready for a new injection stroke.

Figure 11:
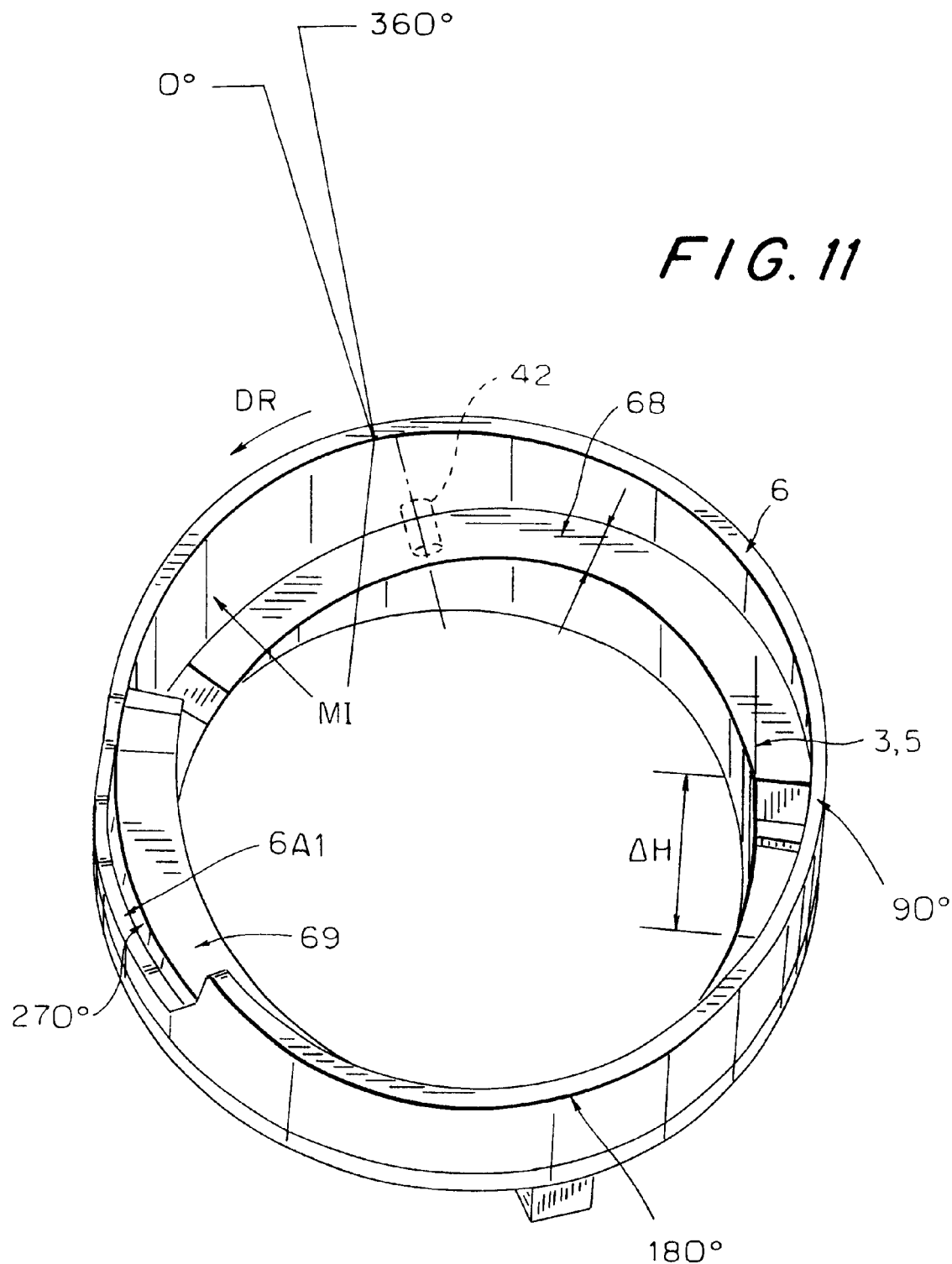
FIG. 11 shows a perspective view of the casing MI of the control sleeve with a control cam.
Figure 12:
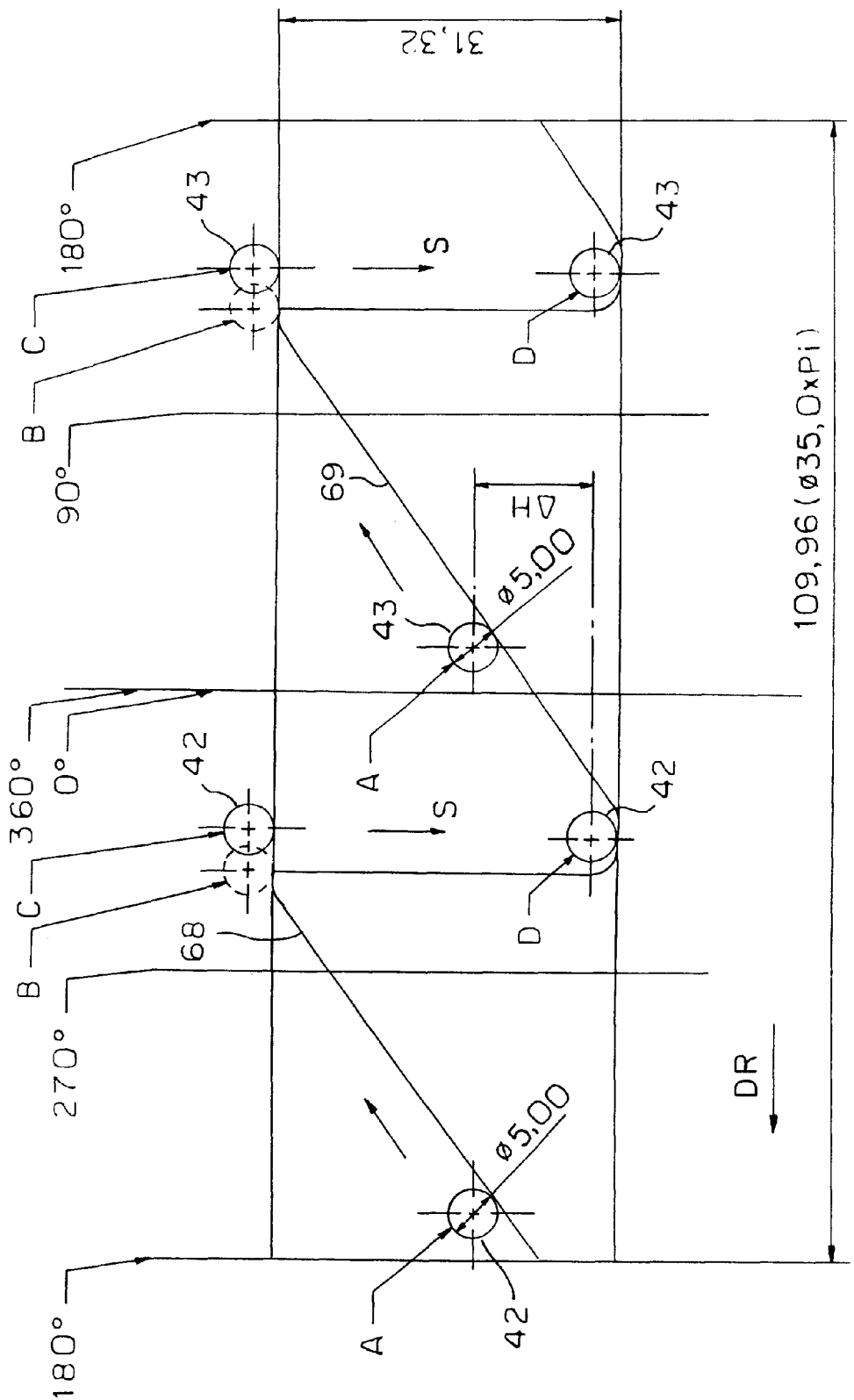
FIG. 12 is a developed view of the inner casing surface MI of FIG. 11 with one control cam.

The design-related implementation of this control principle, then, is explained in detail in two exemplary embodiments:

A preferred implementation of the control-related coupling between the control sleeve 6 and the slide 4 is shown in FIGS. 11 and 12; in this implementation, two structurally identical lifting bolts 42 and 43 are provided, which with profiling in the form of a sawtoothlike control cam cooperate with the control cam portions 68, 69 on the inside MI of the casing of the control sleeve 6. This is a structurally simple version, in which the affects of friction between the lifting bolts 42, 4 and the casing inside MI are merely minimal; because of the perpendicular trailing edges of the portions 68, 69 of the control cam, an unambiguous functional association with the direction of rotation DR exists. Reducing frictional factors leads to a low actuating torque and thus makes for easy manipulation.

An alternative implementation of the control-related coupling between the control sleeve 6 and the slide 4 is shown in FIGS. 13 and 14, in which the same reference numerals are also used for identical parts.

In both implementations of this coupling, the coupling is attained via lifting bolts 42 and 43 of the same or different diameter, which are retained crosswise to the longitudinal axis F in the rear portion 4A of the tappet 4, and which are dimensioned and oriented in the tappet 4 in such a way that a nonpositive engagement is attained between the lifting bolts 42, 43 on the one hand and the control cam portions 64–67 (FIGS. 13 and 14) or 68, 69 (FIGS. 11 and 12) on the other. It is thus possible, by rotating the control sleeve 6, to convert the torque exerted here via the various control cams into a linear restoring force of the tappet 4 counter to the tensing force of the spiral spring 3, so that the tappet 4 and the slide 2 are pushed back in the housing 7 far enough that they regain their respective locking positions A1 and A2. The total counterstroke ΔH executed corresponds in its value to the sum of the two strokes H1 and H2 of the tappet 4 and slide 2. The form of the two control cams shown in the developed view of the inside casing surface MI in FIG. 13 is due to the fact that the implementation of the torque upon rotation of the control sleeve 6 is to be done with the most constant possible torque over the entire counterstroke ΔH, to make the injection device easier to manipulate. Because of the opposed disposition of the two lifting bolts 42, 43, the counterstroke ΔH generated by the control sleeve 6 is transmitted to the tappet or slide in such a way that tilting moments on the tappet and/or slide that could cause canting or seizing are reliably precluded. The distribution of the torque transmission to the two lifting bolts 42, 43 makes a short guide path of the tappet 4 possible and thus a tight, compact design of the injection device in this region.

The design of the control cam portions 64–67 and 68–69 is preferably selected such that the control sleeve 6 can be unmolded from an injection molding tool without difficulty.

Since in the exemplary embodiment of FIGS. 13 and 14 the diameter of the first lifting bolt 42 is significantly less than the diameter of the second lifting bolt 43, the associated control cam portions 64 and 65 do not intersect at an angle of 90° but rather somewhat earlier. This offset of the point of intersection has the result that the lifting bolt 42 which in this exemplary embodiment is spring-loaded executes an axial motion in response to the force acting on it from the spring 44, and already leaves the control cam portion 64 in position 42a and slides on the adjoining control cam portion 67. In this position of the control sleeve 6, the also spring-loaded (spring 45) lifting bolt 43 is still located on the control cam portion 65. This assures that only one lifting bolt at a time will ever be in transition from one control cam portion to the next, so that an assured force transmission from the control sleeve 6 to the tappet 4 always takes place via at least one of the two lifting bolts 42, 43.

Below the positions 42d and 43d shown in FIG. 13, the control cam portions 66, 67 are provided with slide ramps 61, 62, by way of which the lifting bolts 42, 43 return to their outset position (parallel arrows S in FIG. 13).

A further design-related implementation of the control principle by means of the control sleeve 6 relates to securing the injection device in the locking position of the tappet 4, depending on the angular position of the control sleeve 6:

For this purpose, two mutually opposite securing pawls 41 are integrally formed as securing means on the rearside of the guide portion 4A of the tappet 4 and, when the control sleeve 6 is in the opening and securing position P2, said securing pawls are in releasable engagement with two control pawls 53 and 54, displaceable transversely to the operating direction F, of a trigger means and thus hold the tappet 4 in its locking position A2 counter to the pretension of the helical spring 3. In the exemplary embodiment illustrated, the engagement described is such that the two securing pawls 41 have noses which point in the same direction and which slide over the rear surfaces of the control pawls 53,54 into the locking position, for which purpose the control pawls have ramp like slopes, so that engagement causes the securing pawls 41 to snap in elastically over the control pawls 53, 54, as illustrated in FIG. 1.

The control pawls 53 and 54 are part of a trigger means which is led outward through the housing 7 in the handling portion 7A of the latter and is designed as an actuating button 5. This actuating button 5, together with the control pawls 53 and 54, can be moved in the housing 7 counter to a spring 51 which ensures that securing engagement, illustrated in FIG. 1, between the tappet 4 and trigger means is maintained.

Cooperation between the actuating button 5 and control sleeve 6, then, is such that the actuating button 5 can be displaced (and consequently the securing pawls 41 released) only transversely to the operational axis F, when the control sleeve 6 is in its closing and operating position P1. Since this closing and operating position P1 is defined unequivocally by the angular position of the control sleeve 6 on the housing 7 (cf. FIG. 2), this control coupling between the actuating button 5 and control sleeve 6 is achieved in a simple way, in that the rear edge region of the control portion 6A of the control sleeve 6 extends at the rear 35 over a nose 5A of the actuating button 5 (engages behind said nose) and, only in the corresponding angular sector which corresponds to the closing and operating position P1, has an edge recess 6A1 (FIG. 11), through which the nose 5A of the actuating button 5 can pass in the closing and operating position P1. Consequently, when the control sleeve 6 is in the operating and closing [sic] position P1, the locking position A2 of the tappet 4 can be canceled, in that the actuating button S is pressed into the housing 7 and, consequently, the control pawls 53, 54 release the two securing pawls 41, with the result that the helical spring 3 can then immediately exercise its force and the two strokes H1 and H2 are executed in succession, as described initially.

For the unequivocal definition of the two positions P1 and P2 of the control sleeve 6, there is provision, furthermore, for the front conically tapering guide portion 6C of the control sleeve 6 to have mutually opposite, inwardly directed, dish-shaped recesses 77A and 77B which are in interaction with a spring-loaded catch element 77 held in the housing 7. When the control sleeve 6 is in the opening and securing position P2 illustrated in FIG. 1, the catch element 77 is in engagement with the recess 77A, and, in the closing and operating position P1 illustrated, for example, in FIG. 8, the catch element 77 is therefore in engagement with the depression 77B.

The brief, active rotation of the control sleeve 6 brought about by this catch mechanism thus ensures that the two basic positions P1 and P2 of the control sleeve 6 are detected by the user's senses and consequently also serves, as it were, as a feedback of the current operating state of the injection device, thus further increasing the operating safety.

Proper, reliable functioning of the injection device is already possible by means of the structural operating parts described above, but, for further refinement and improvement, other means are also provided which are additionally presented briefly below:

A rotation damper 100 of a commercially available type, which is connected to the housing 7 via a rack 101, is provided in the slide 2. This is a rotation damper, such as is obtainable, for example, under the product designation FRT-C2 from the company ACE Sto8dampfer GmbH of D-40764 Langenfeld. Such a rotation damper 100 operates essentially by the interposition of a means of specific viscosity in the relative movement between the body and the rack 101, so that a force acting between these two components causes lower acceleration during the resulting linear displacement. In the injection device, the functioning of the rotation damper 100 is selected in such a way that the acceleration of the slide 2 during the first stroke H1 (that is to say, with the high tension force of the spring 3) is limited to a desired value which, on the one hand, still ensures reliable, rapid pricking of the injection needle 13 into the tissue, but, on the other hand, avoids overly apparent abutting effects, such as jolts and vibrations at the end of the first stroke H1, so that generally "smoother" operation is achieved during injection.

In order to make handling easier when the syringe 1 is extracted after the injection operation has ended, an ejection means is provided opposite the loading orifices L6, L7 of the housing 7 and of the control sleeve 6 (that is to say, to that extent "below" the syringe 1), said ejection means being activated during the opening of the injection device (rotation of the control sleeve 6 from the closing and operating position P1 into its opening and securing position P2), to the effect that said ejection means lifts the rear end of the syringe 1, as it were, toward the user and makes extraction easier. Here, too, the function of the control sleeve 6 as a control means should be emphasized again, in that specific functions or additional functions are activated or made possible solely as a result of the actuation of the control sleeve.

Figure 15C:
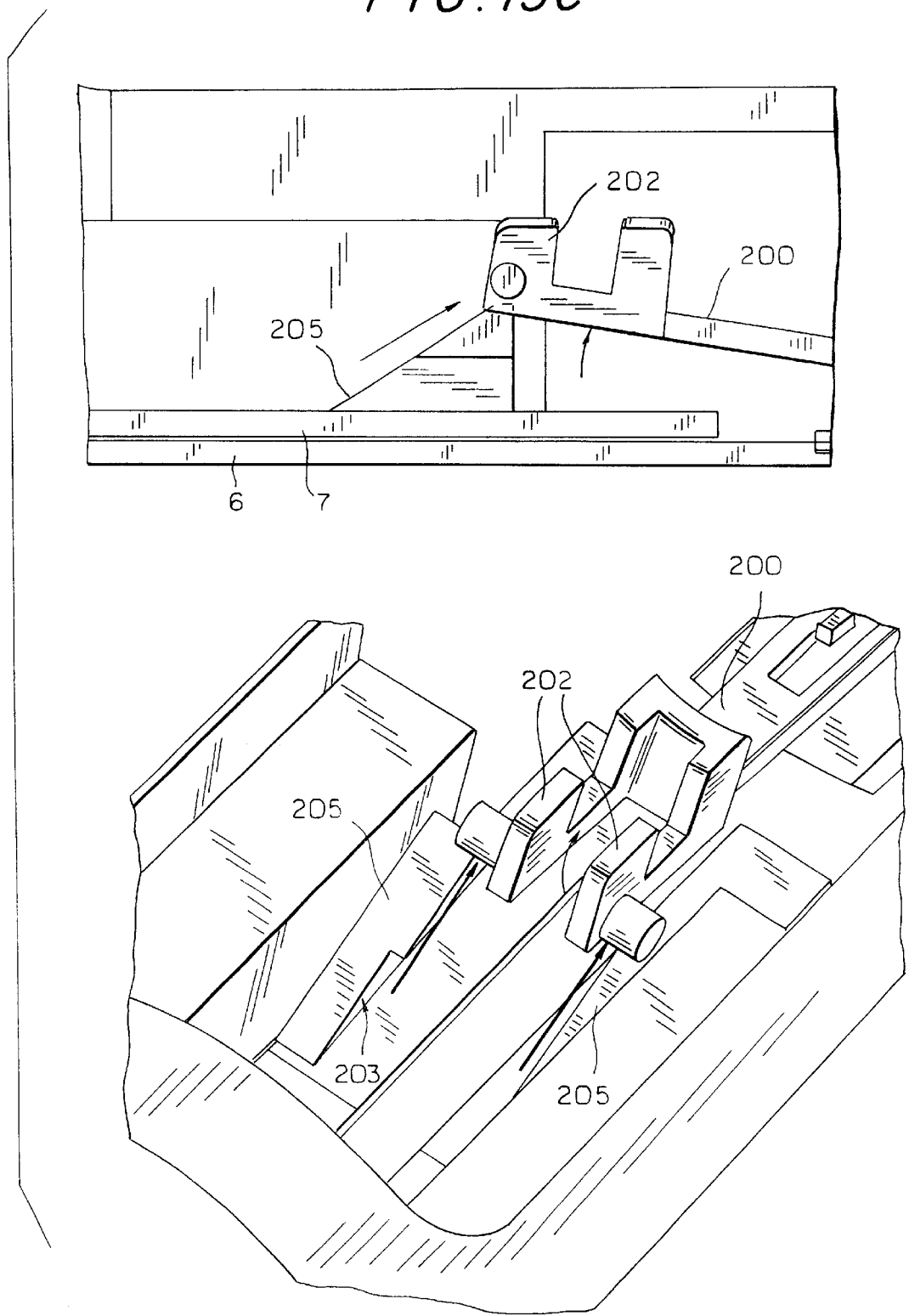
Figure 16A:
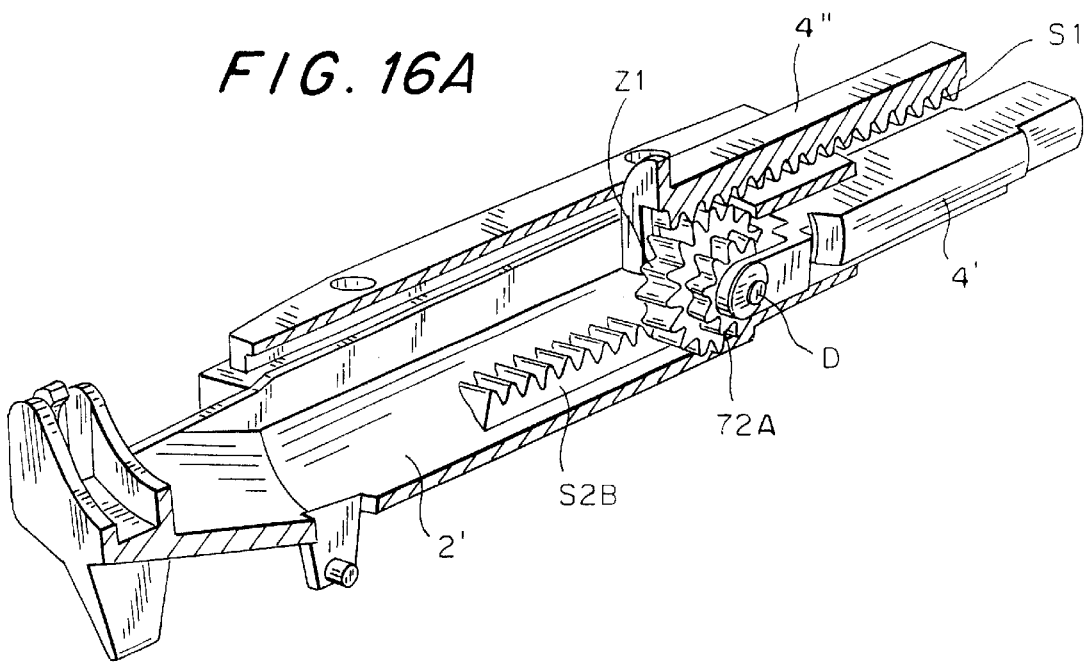
Figure 16B:
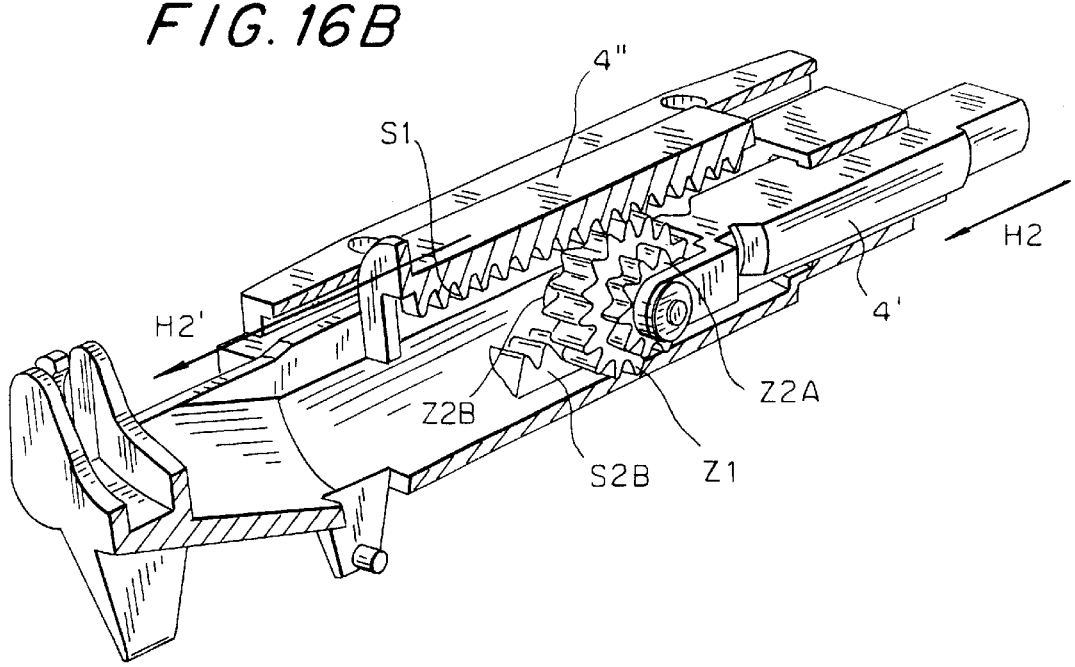
Figure 16C:
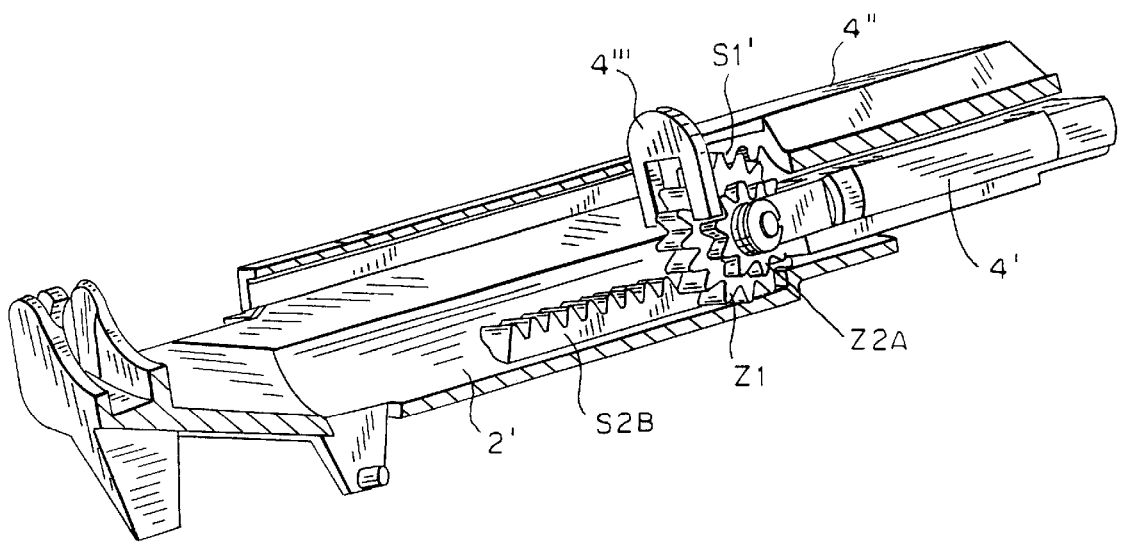
Figure 16D:
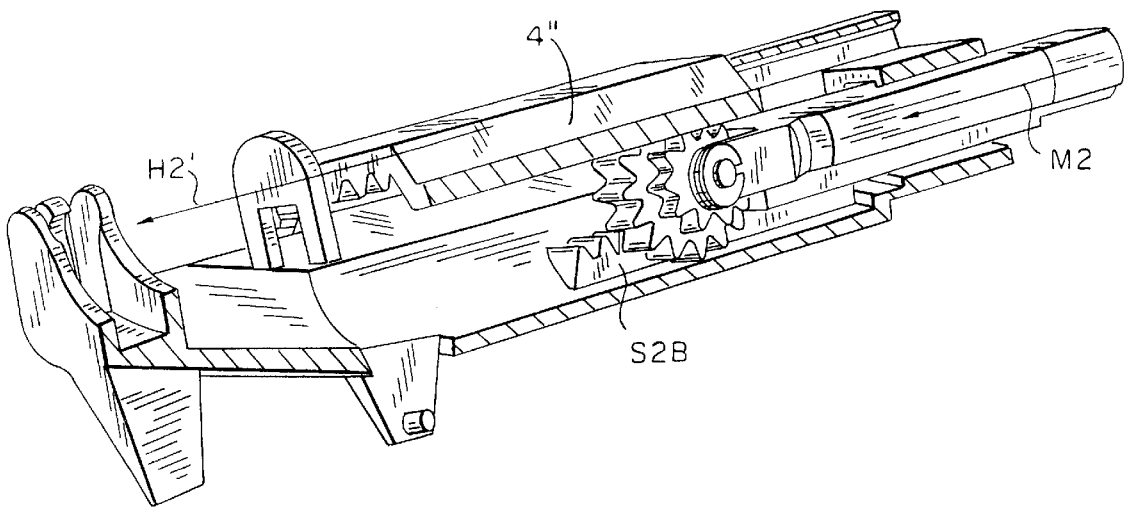

The ejection means (see, in particular, FIG. 15 in this respect) contains, initially, an ejection lever 200, one leg end of which is held pivotably on the slide 2 by means of a pin 201, in such a way that its other leg end angled at 90° can be moved in the direction of the syringe 1. For this purpose, the slide 2 has a corresponding recess or slope 2C which at the same time also defines the pivoting angle of the ejection lever 200. The ejection lever 200 has, in the same plane as its first leg, a control boss consisting of two sliding bosses 202 which are arranged in a fork like manner which are guided in a guide channel 203 narrowing in the stroke direction, until their ends pointing outward in a hook like manner come into engagement with the lower end of a guide track 205 when the first stroke is terminated. The guide track 205 rises in the direction of the longitudinal axis F in a ramp like manner opposite to the injection direction and is positioned and oriented in such a way that, when the control sleeve 6 is rotated into its opening and securing position P2 and the slide 2 is consequently moved back into its locking position A1, the two sliding bosses pass onto this guide track 205 and the ejection lever 200 is therefore guided upward, so that the ejection movement is concluded when the control sleeve 6 has reached its opening and securing position P2.

As another additional means, the injection device has a signal means which is actuated at the end of the second stroke H2 after injection has taken place. There is provision, in this case, for this signal means to consist solely of mechanically acting structural elements and, by means of a bell 306, to emit an acoustic signal, in order to generate which there is a striking pin 305 which is movable transversely to the longitudinal axis F and which loads the edge region of the bell 306 in a pulse like manner.

Figure 4:
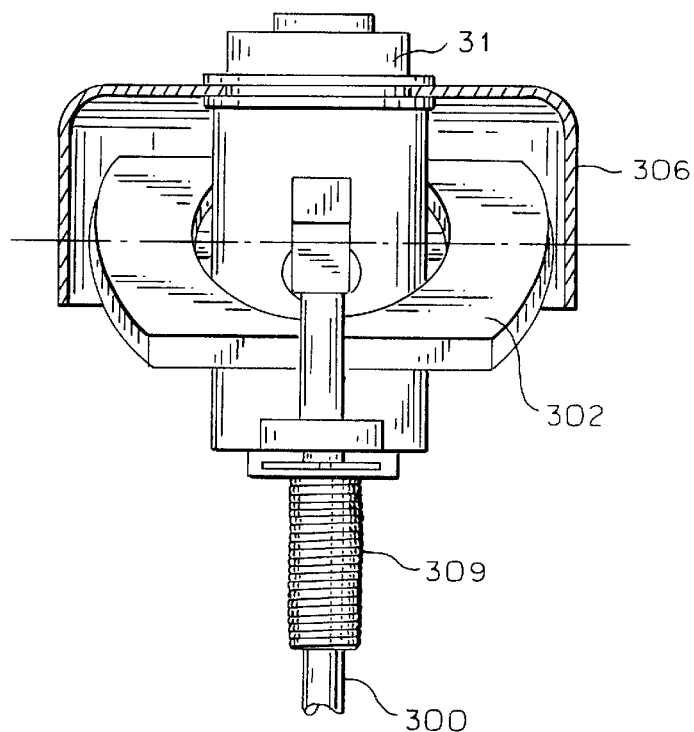
FIG. 4 shows a first side view of the signal means of the injection device, in the sectional plane of FIG. 1.
Figure 5:
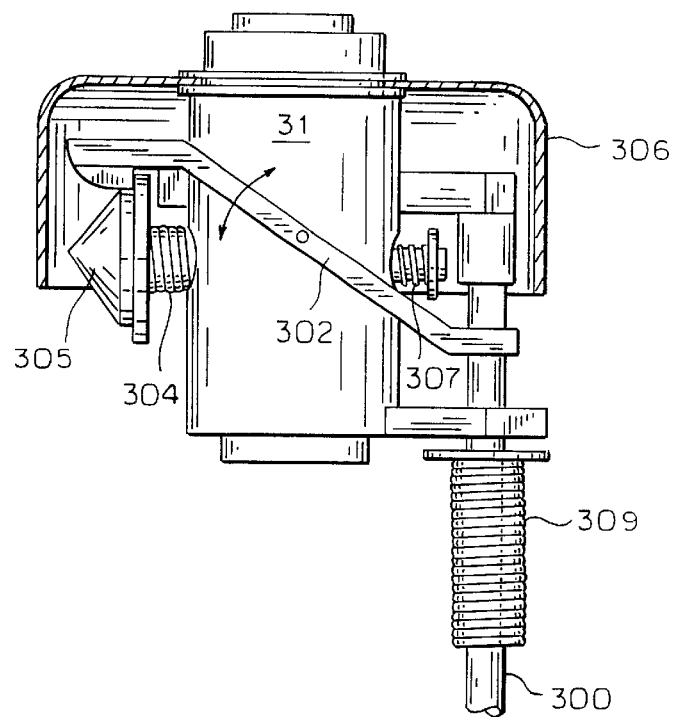
FIG. 5 shows a second side view of the signal means of the injection device, in the sectional plane of FIG. 3.

The detailed design of the signal means is illustrated especially in FIGS. 3, 4 and 5:

One end of a tension rod 300 is held movably in a bore of the tappet 4, the other end of said tension rod engaging on a collar like yoke 302 held on the holding block 31 which is fastened in the rearside 74 of the housing and which serves, on its front side, as an abutment for the helical spring 3. The bell 306 is also held on this basic body 31 by means of a circumferential groove, so that said bell covers the yoke 302. The axis of rotation 303 of the yoke 302 runs, in this case, through the longitudinal axis F perpendicularly to the drawing plane of FIG. 3. At its end facing away from the tension rod 300, the yoke 302 engages over an edge groove of the striking pin 305 which is fixed in the locking position by a tongue 308 of the tappet 4. The striking pin 305 is held forcibly in the drawing plane of FIG. 3 by means of two springs 304 and 307. The tension rod 300 is surrounded by a compression spring 309 which ensures that the yoke 302 remains in the catch position illustrated in FIG. 3

The length of the tension rod 300 is selected in such a way that, at the end of injection (FIG. 10), the tappet 4, via an abutment 301, loads the tension rod 300, so that the latter, in turn, pivots the yoke 302, whereupon the opposite end of the yoke 302 releases the circumferential catch of the striking pin 305, so that, under the coordinated force of the two springs 304, 307, the striking pin 305 (already released by the tongue 308) is thrown against the inner edge region of the bell 306, as illustrated in FIG. 10. The spring constants of the springs 304 and 307 are, in this case, dimensioned in such a way as first to ensure that the striking pin 305 reaches the bell 306 in order to trigger the acoustic signal, but the spring 307 then draws the striking pin 305 back again, so that the bell can vibrate freely, without damping effects caused by the striking pin 305 resting on it, and can generate the typical sound of a clapper-actuated bell. When the tappet 4 returns to its locking position, the sloping end of the tongue 308 slides onto the tip of the striking pin 305 again and presses the latter back until the detent pawl of the yoke 302, then loaded again by the compression spring 309, engages over the edge groove of the striking pin 305 and secures the latter.

Now that the structural preconditions have been presented in detail, their functioning will also be described briefly, step by step, with reference to a complete injection operation:

The position and arrangement of the structural parts, as illustrated in FIGS. 1 to 3, is selected as the starting position:

Here, the control sleeve 6 is in its opening and securing position P2, that is to say a syringe 1 can be inserted through the loading orifices L6 and L7 into the position provided for it in the slide 2. At the same time, the control sleeve 6 is held in the opening and securing position P2 by the catch element 77 penetrating into the recess 77A.

The two lifting bolts 42, 43 are in their position B (FIG. 12) or in the uppermost position 42c, 43c, illustrated in FIG. 13, on their associated control cam portions.

The tappet 4 and slide 2 are in their rear locking position A1 and A2, since the securing pawls 41 are in engagement with the two control pawls 53 and 54 and activation of the trigger means is not possible, since the nose 5A of the actuating button is blocked by the edge region of the cylindrical control portion 6A of the control sleeve 6.

The tongue 308 on the guide portion 4A of the tappet 9 has its rear end face in contact with the conical striking pin 305, and the detent pawl of the yoke 302 is pressed by the force of the spring 309 over the peripheral edge of the striking pin 305 and retains the latter. The activation of the bell 306 is therefore likewise not possible in this position. The spring 3 is in its compressed, that is to say ready-to-act state.

When the syringe 1 is inserted with its protective cap 11 into the slide 2 and is fixed by means of its syringe collar 12, the control sleeve 6 is rotated through 180° with one hand by the user, the user's other hand retaining the handling portion 7A of the housing 7. The loading orifice L7 of the housing 7 is thereby closed by the control sleeve 6 and the closing and operating position P1, illustrated in FIG. 9, of the control sleeve 6 is consequently assumed. In this position, the contact element 77 then penetrates into the depression 77B in the control sleeve 6 and the lifting bolts 42, 43 are in position C (12) or position 42d; 43d (13). The recess 6A1 in the rear edge region of the cylindrical control portion 6A simultaneously comes into the region of the nose 5A of the actuating button, so that the injection device can consequently be used in the closing and operating position P1.

For this purpose, first the protective cap 11 is removed from the needle 13 of the syringe 1 and the injection device is applied to the intended place of injection. After proper positioning, the trigger means is then activated, that is to say the actuating button 5 is pressed into the housing 7, with the result that, after a short travel in the millimeter range, the control pawls 53, 54 release the two securing pawls 41.

As soon as this has taken place, the spring 3 can exercise its effect and presses forward the tappet 4 and slide 2 still connected nonpositively to one another via the coupling element 8, that is to say, under the delaying effect of the rotation damper 100, the first stroke H1 is executed, causing the injection needle 13 to prick into the tissue. During this movement of the slide 2, the ejection lever 200, which is held in the slide 2 via the pin 201, moves with its sliding bosses 202 on the track 203. As a result of the narrowing track 203, the two legs 204 are pressed inward, so that, toward the end of the first stroke, tension is generated, by means of which the sliding bosses 202 jump outward and come into engagement with the guide track 205.

Moreover, in the exemplary embodiment shown in FIGS. 13 and 14, at the start of the first stroke H1, the lifting bolts 42, 43 loaded by the springs 44, 45 slide over the sliding ramps 61, 62 into the free space 63. As explained above, the end of the first stroke H1, which the slide 2 and the tappet 4 execute jointly, is defined in that the coupling element 8, when it slides along on the inner surface of the housing 7, finally reaches the catch element designed as a depression 72. By virtue of the transmission of force via the sloping surfaces of the depressions, the coupling element 8 slides into the depression 72, with the result that the positive connection and nonpositive connection between the tappet 4 and slide 2 is canceled and the slide 2 has then arrived in its front end position in the housing 7 and is fixed positively. The injection needle 13, too, has consequently reached its foremost position in the longitudinal axis F.

Figure 6:
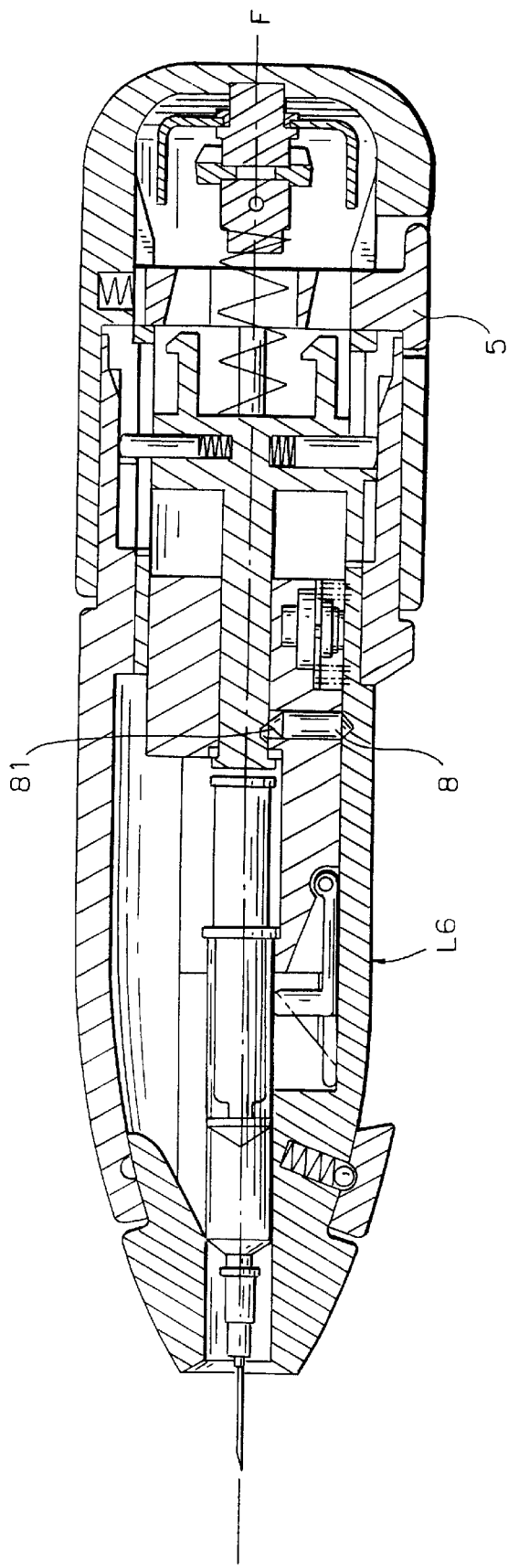
FIG. 6 shows a third longitudinal section through the injection device directly at the start of the second stroke, in the plane of FIG. 1.

Under the action of the spring 3, then, the tappet 4 alone executes the second stroke H2, FIG. 6 illustrating directly the start of the second stroke when the recess 81 in the tappet 4 moves away from the coupling element 8 which is now held in the housing 7.

Figure 7:
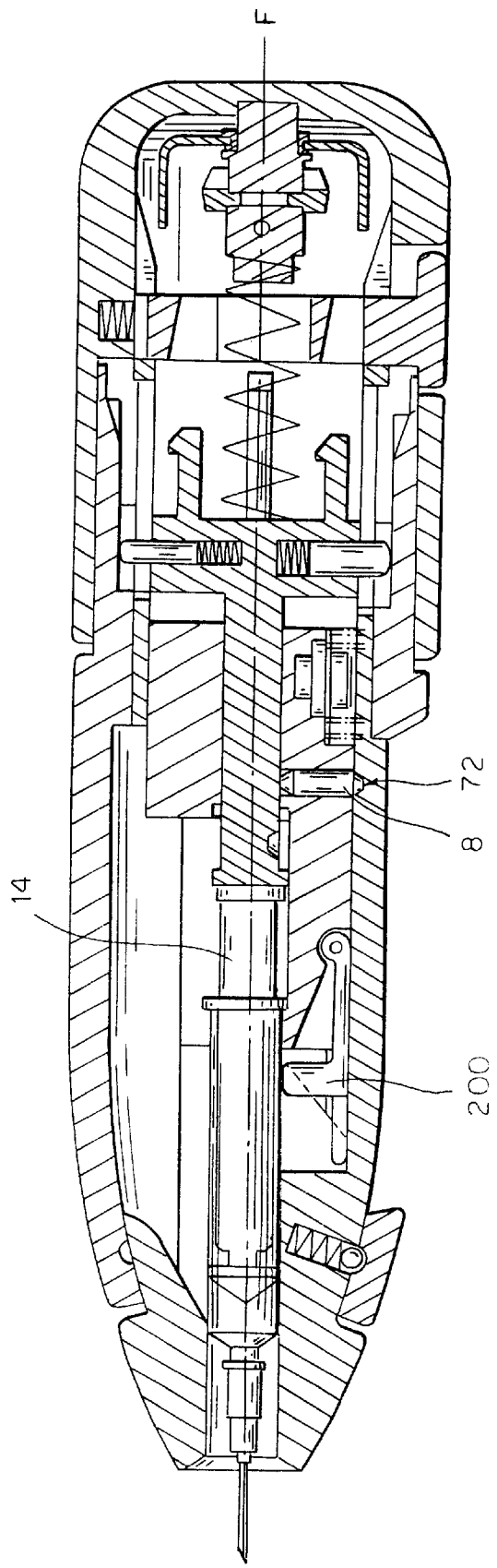
FIG. 7 shows a fourth longitudinal section through the injection device during the second stroke, in the plane of FIG. 1.

As the second stroke continues, the front side of the tappet 4 loads the plunger 14 of the syringe 1, presses said plunger into the syringe and thus causes the injection fluid to be injected; this position toward the end of the second stroke is illustrated in FIG. 7.

At the end of injection, that is to say when the tappet 4 has reached its front end position, it actuates the tension rod 300 via the abutment 301 (FIG. 10), as a result of which the catch of the striking pin 305 is released via the lever 302. Under the action of the spring 304, said striking pin butts onto the inner edge region of the bell 306, so that the sound initially mentioned, which is clearly detectable by the instrument user, is generated. Under the counteraction of the spring 307, the striking pin 305 is drawn back from the bell immediately after this action, so that the bell can vibrate freely.

The user, then, has obtained information on the termination of the injection operation and can consequently lift off the injection device from the place of injection and draw the injection needle 13 out of the tissue.

In order to extract the syringe 1, then, the control sleeve 6 is again moved through 180° from its closing and operating position P1 into the opening and securing position P2 (FIG. 2), so that the syringe 1 becomes accessible again. This rotation of the control sleeve 6 initially has the effect that, by means of the control cam portions 64 to 67, in cooperation with the lifting bolts 42, 43, the rotational movement through 180° is converted into the counterstroke ΔH of the tappet 4 (which precautions, not illustrated, prevent from executing a radial movement). When the rear abutment 46 reaches the slide 2 again, the coupling element 8 slides out of engagement with the housing 7 again and the slide 2 is coupled to the movement of the tappet 4 again.

During this first portion of the return movement of the slide 2, the sliding bosses of the ejection lever 200 move, with the slide 2, obliquely upward on the guide track 205, so that, in this region, the rotation of the control sleeve 6 is converted into a rotational movement of the ejection lever 200 which finally 10 engages under the syringe 1 and lifts it up when the rotation of the control sleeve 6 has ended.

Toward the end of this rotational movement, the sloping ends of the securing pawls 41 slide on the corresponding slopes of the two control pawls 53 and 54, until, at the end of this operation, the spring-loaded trigger means catches again with its control pawls 53, 54 behind the rear flanks of the two securing pawls 41, before the two locking positions A1 and A2 of the tappet 4 and slide 2 are then finally assumed again.

Simultaneously with this operation, the tongue 308 also penetrates again through the associated orifice in the trigger means. By virtue of the correspondingly sloping contact surfaces between the tongue 308 and striking pin 305, the axial movement of the tongue 308 is 30 converted into a corresponding transverse movement of the striking pin 305, until the latter finally again reaches a position where the tension rod, which in the meantime has been pressure-loaded again by the compression spring 309, can pivot the lever 302 in such a way that the opposite end of the latter catches again on the circumferential edge of the striking pin 305.

The syringe 1 can then be extracted and the injection device is stored, in this state, until its next use.

However, rotation of the control sleeve 6 is likewise possible, so that the operations as described above can also be carried out "idly". At all events, the rotation of the control sleeve 6 through 180° into its opening and securing position P2 causes loading of the tappet 4 and of the slide 2 and the return of these into their locking position, so that the injection device is then ready for receiving a new syringe 1.

In order to illustrate the last-mentioned conversion of the rotational movement of the control sleeve 6 into the axial displacement of the tappet and slide back into their locking position, these sequences will be explained once again with reference to FIGS. 11 and 14:

In the preferred exemplary embodiment (FIGS. 11 and 12), after injection has taken place, the two lifting bolts 42, 43 are in their lowermost position D; upon rotation of the control sleeve 6 in the direction DR, the two lifting bolts slide in the direction of the obliquely upward-oriented arrows to "their" portion 68, 69 of the control cam and in the process execute the counterstroke ΔH. On reaching the apex of the control cam portions 68, 69 (position B) after a rotation about approximately 180°, the locking positions of the tappet 4 and slide 2 are again attained. Upon further rotation of the control sleeve 6, again by 180°, the lifting bolts then reach position C, in which the detent locking is also effected by means of the detent element 77/recess 77A, and the change of syringes can be made. After reactivation of the injection device, the two lifting bolts move (arrows S) over the vertical flank of their control cam portion 68, 69, after the termination of the injection process, back to their position D.

In the second exemplary embodiment, having two control cams (FIGS. 13 and 14), after injection has taken place, that is to say at the end of the two strokes H1 and H2, the first lifting bolt 42 is at the lowest point of its associated control cam 64 and, correspondingly, the second lifting bolt 43 is at the lowest point of its associated control cam 65. When the control sleeve 6 is rotated in the direction of the arrow DR, then, the two lifting bolts 42, 43 slide relatively in the opposite direction (small arrows directed obliquely upward) on the control cams 64 and 65 and, at the same time, execute the counter stroke ΔH which is directed opposite to the two strokes H1 and H2 when injection is being carried out. For each rotary angle unit of the control sleeve 6, the control cam 64 or 65 runs relatively steeply, since, here too, the spring 3 is still largely in its detensioned position and therefore opposes only a little force to the corresponding counter stroke of the slide 2 and tappet 4 during the rotation of the control sleeve 6. The shape of the control cams 64 and 65 is therefore a direct mirror image of the increasing force of the spring 3 counteracting the counterstroke ΔH, and optimization can be achieved insofar as, for each angle unit of the rotation of the control sleeve 6, an approximately equal torque has to be exerted by the user, thus ensuring convenient handling. This means, conversely, that rotation of the control sleeve 6 through a fixed rotary angle at the start of rotation leads to a greater corresponding counterstroke than at the end of the rotational movement, where the virtually full tension force of the spring 3 demands a very flat run of the control cam portions 66, 67.

By virtue of the offset of the intersection points of the control cam portions 64, 67 and 65, 66, as a result of the force acting by means of the spring 44 on the first lifting bolt 42 the latter executes an axial movement, during which, in the position 42, it leaves 15 its control portion 64 and slides onto the control portion 67. At this moment of transition, however, the second lifting bolt 43 is still located on its control cam portion 65, so that the transmission of torque from the control sleeve 6 to the tappet 4 remains guaranteed.

In the position 42b, 43b, after a rotation of the control sleeve 6 of somewhat less than 180°, the two lifting bolts 42, 43 have generated the necessary counterstroke ΔH of the tappet 4, said counterstroke corresponding in amount to the sum of the two strokes H1 and H2, as illustrated in FIG. 13, and the locking position of the tappet 4 and, consequently, the slide 2 is reached. The control sleeve is then rotated somewhat further, until, and only then, the already above mentioned catching of the catch element 77 in the recess 77A is brought about again, thereby also telling the user that locking is now ensured again and the empty syringe 1 can be extracted and, if appropriate, a new one inserted again. The two lifting bolts 42, 43 assume the position 42c, 43c.

At the transition of the control sleeve 6 from its opening and securing position P2 into its closing and operating position P1, the two lifting bolts 42 and 43 are again guided through 180° into their original angular position at 42*d* and 43*d*, but so as to be offset by the amount of the sum of the two strokes H1 and H2; only when the injection device is activated by the trigger means, now becoming possible again, do the two lifting bolts, via the sliding ramps 61, 62, again reach the position, presupposed at the outset of the operating description, at the lower vertex of their associated control cam portions after injection has ended.

In FIGS. 16–19, an especially preferred embodiment of the slide is shown in cooperation with a gear. As a result of this concept of a "gear slide", it becomes possible to adapt the second stroke H2, which is predetermined in the above-described exemplary embodiment, in terms of its value to the injection stroke of a special syringe, since not all syringes used are standardized with regard to this value. By the choice of a suitable gear, it is accordingly possible, on the basis of the stroke H2 of the tappet 4', to generate a stroke H2' that is shorter step-down gear ratio) or longer (step-up gear ratio) than the stroke H2 of the tappet 4'.

In the exemplary embodiment shown in FIGS. 16–19, a gear with a gear step-up ratio is shown, that is, the injection stroke H2' is longer than the stroke H2 of the tappet 4'. It should be especially noted here that the two strokes H2 and H2' are in the same direction, for instance in contrast to versions (DE 28 12 729 A1), where although a gear version is also claimed, the actuation stroke and injection stroke are oriented contrary to one another.

The structural attainment of this embodiment concept will now be described in further detail:

The slide 2' is embodied in the manner of a tub and guides the tappet 4' on the one hand but on the other hand also guides a thrust rod 4" parallel to one another. The thrust rod 4" has a first rack S1 on its underside, while a pressure plate 4''' is formed onto the front side and acts on the syringe plunger 14 of an injection syringe 1 which is held in the syringe receptacle by its collar 12.

On its end located in front in the injection direction, the tappet 4' in forklike fashion includes an arrangement of a total of three gear wheels, having a middle, first gear wheel Z1 which meshes with the rack S1 of the thrust rod 4", and two gear wheels Z2A, Z2B of lesser diameter, which are secured coaxially on both sides of this central, first gear wheel Z1 and mesh with a respective rack S2A and S2B on the bottom of the slide 2'.

The two racks S2A, S2B on the bottom of the tublike slide 2' are spaced apart far enough that the gear ring of the first gear wheel Z1 can protrude between these two racks.

In the preferred exemplary embodiment shown in FIGS. 6–19, the first gear wheel Z1 thus consequently meshes with the rack S1 on the underside of the thrust rod 4", and the two laterally disposed second gear wheels Z2A/Z2B each mesh with their respective associated second rack S2A/S2B.

In the exemplary embodiment shown in the drawings, what is involved is consequently a gear step-up ratio; that is, the second stroke H2 of the tappet 4' is converted into a stroke H2' of the thrust rod 4" that is more than twice as long as the second stroke H2.

Figure 17A:
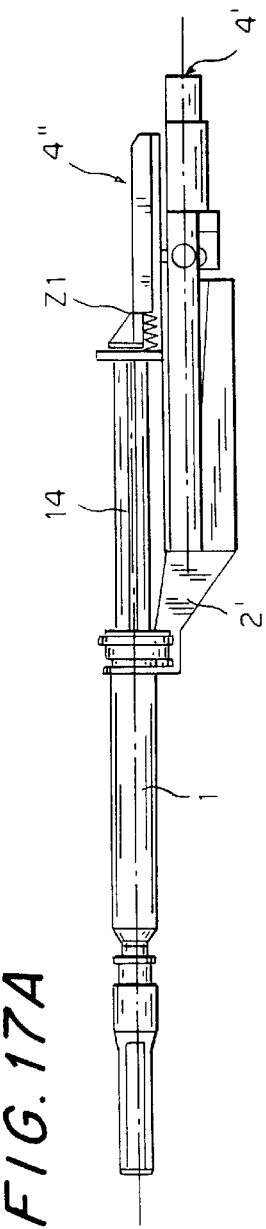
Figure 17B:
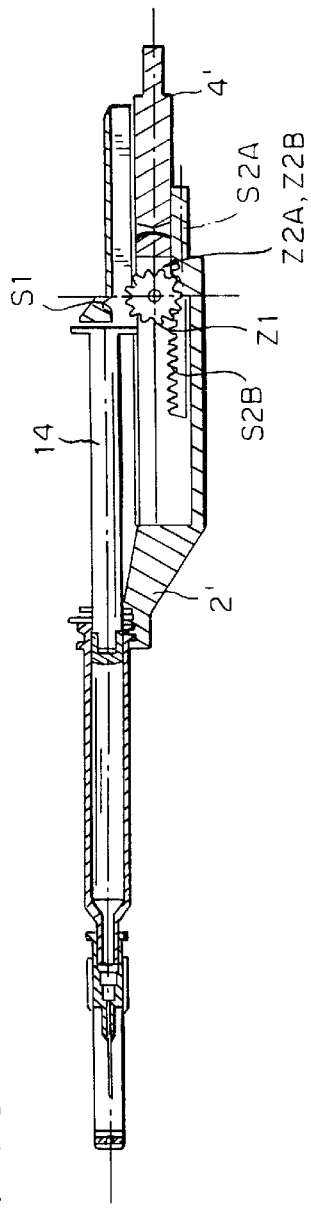
Figure 17C:
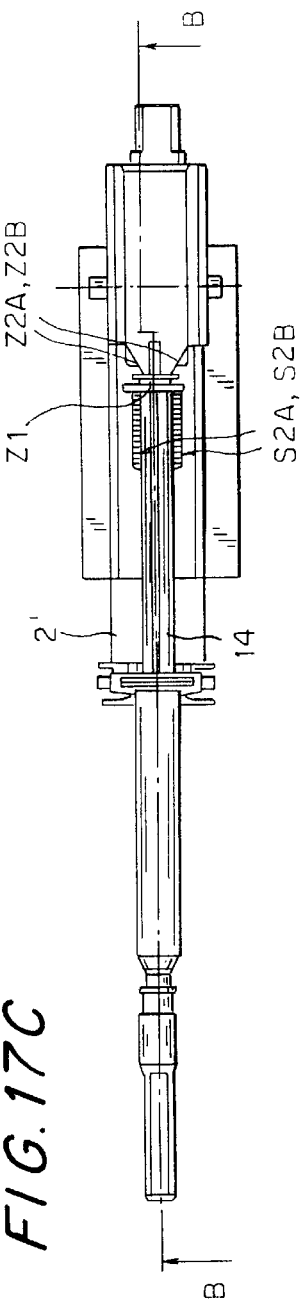

With this device, space is accordingly made in particular for injection syringes 1 that have a very long injection stroke and a correspondingly long syringe plunger 14, as is shown particularly clearly in FIGS. 17.

Figure 18:
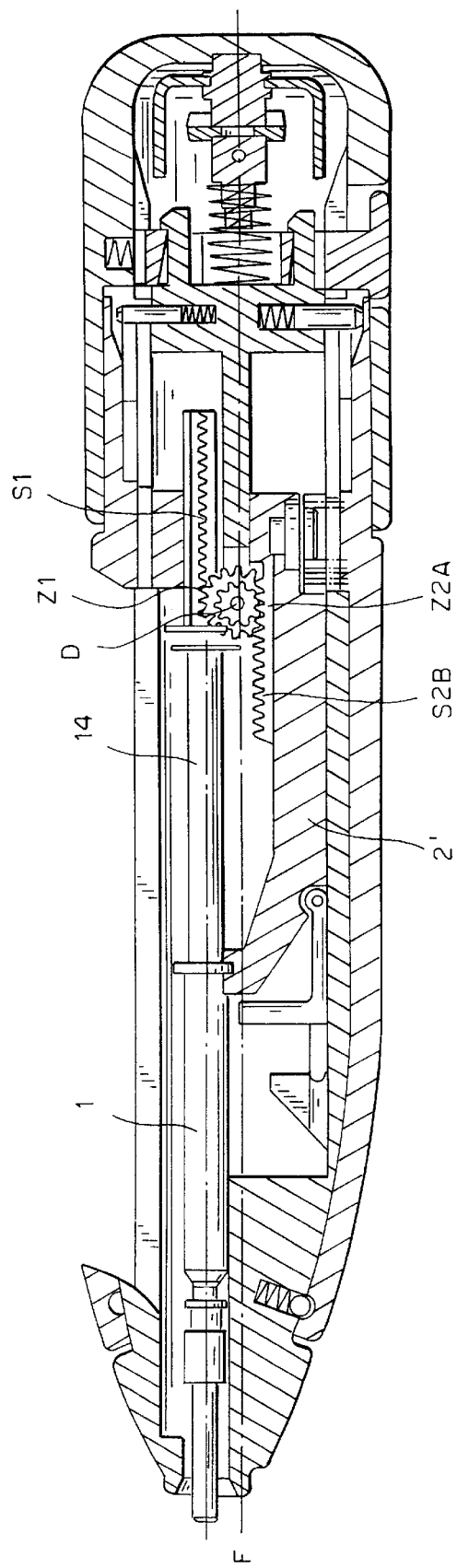
FIG. 18 shows the injection device with the built-in gear slide.
Figure 19:
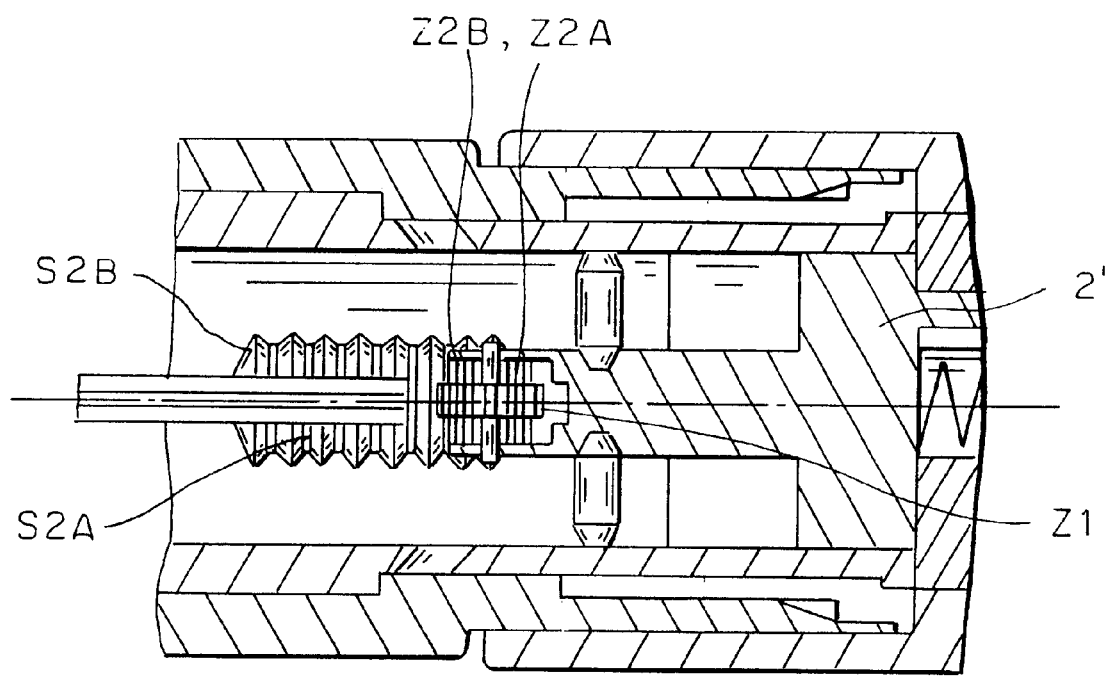
FIG. 19 is a horizontal fragmentary section through the injection device in the region of the gear slide.

The overall concept and the mode of operation of the slide 2' as such in interaction with the other components of the injection device is filly preserved here, as clearly shown in FIGS. 18 and 19, where instead of the carriage 2 in the exemplary embodiments described above, the "gear slide" 2' is built in. The only resultant change is that because of the corresponding structural height, which is approximately equivalent to the radius of the first gear wheel Z1, a corresponding deviation of the injection axis from the longitudinal axis F of the housing is brought about, which can be taken into account by suitable simple predetermined dimensions on the housing.

Particularly from the isolated view of the "gear slide" 2' in FIGS. 16 and 17, it becomes clear that such a version is not limited to the injection device as described in its details at the outset, but also can be used or employed in injection devices of a conventional design, by making simple modification. For instance, in such a simple case, the slide 2' can be connected in stationary fashion to a simple housing, and the tappet 4' can be provided, on its side remote from the injection direction, with an actuating end that protrudes out of this housing, so that here the simplest case of a syringe actuation is made possible, with the desired step-up of the actuating stroke to an injection stroke oriented in the same direction.

What is claimed is:

1. An injection device for actuating a syringe, in particular a disposable syringe, with drive and control means which are held in a housing and which cause the injection operation to take place successively in such a way that first a linear displacement of the syringe (1) with the injection needle takes place for introducing the injection needle into the skin, and then the injection of the injection fluid takes place, and the drive and control means contain a control sleeve (6) which is displaceable between a closing and operating position (P1), which prevents access to the syringe (1) and releases a trigger means for the injection operation, and an opening and securing position (P2), which allows the syringe (1) to be inserted and extracted, characterized in that the control sleeve (6), over part of its circumference, has a loading orifice (L6) for inserting and extracting the syringe (1), and that it is rotatable between the closing and operating position (P1) and the opening and securing position (P2) by a control angle (a) on the casing surface (M) of the housing (7).

2. The injection device as claimed in claim 1, characterized in that the control sleeve (6) has a substantially cylindrical middle portion (6B), which has the loading orifice (L6).

3. The injection device as claimed in claim 1, characterized in that the housing (7) has an essentially cylindrical middle portion (7B) which has, over part of its circumference, a loading orifice (L7) for inserting and extracting the syringe (1).

4. The injection device as claimed in claim 2 characterized in that the housing (7) has an essentially cylindrical middle portion (7B) which has, over part of its circumference, a loading orifice (L7) for inserting and extracting the syringe (1) and in that the two loading orifices (L6, L7) extend over part of the respective circumference of their associated structural part (6, 7), the circumferential angle ($\alpha 1$, $\alpha 2$) of which is greater than 180°, so that, in the closing and operating position (P1), the syringe (1) is surrounded completely by the housing (7) and the control sleeve (6) and, when the control sleeve (6) is in the opening and securing position (P2) rotated through the control angle ($\alpha$) the two loading orifices (L6, L7) are at least partially congruent.

5. The injection device as claimed in claim 1, wherein a first stroke (H1) of a slide (2), in which the syringe (1) is held for introducing the injection needle (13) is provided, within the housing (7), between a locking position (A1) and an advanced position (V1).

6. The injection device as claimed in claim 5, characterized in that a second stroke (H2) of a tappet (4) in the operational axis (F) relative to the slide (2) for injecting the injection fluid is provided, within the housing (7), between a locking position (A2) and an advanced position (V2).

7. The injection device as claimed in claim 6, characterized in that the relative positions of the tappet (4) and slide (2) are defined by a coupling element (8), in such a way that, after the trigger means has been actuated, the second stroke (H2) of the tappet (4) directly follows the first stroke (H1) of the slide (2) and the two strokes (H1, H2) are added together.

8. The injection device as claimed in claim 7, characterized in that, during the first stroke (H1) of the slide (2), the coupling element (8) couples the latter and the tappet (4) to one another via a first catch element (81) in the tappet (4) and, after the first stroke (H1), releases the coupling by means of a second catch element (72) in the housing (7), so that the tappet (4) alone then carries out the second stroke (H2).

9. The injection device as claimed in claim 1, characterized in that the control sleeve (6), housing (7), slide (2) and tappet (4) are designed at least in portions, as cylindrical or hollow-cylindrical portions lying coaxially to one another.

10. The injection device as claimed in claim 9, characterized in that the housing (7) has, in a rear cylindrical handling portion (7A), an annular groove (75), in which a cylindrical control portion (6A) of the control sleeve (6) is guided rotatably.

11. The injection device as claimed in claim 10, characterized in that the control sleeve (6) has a front tapered guide portion (6C) which is held rotatably on the housing (7).

12. The injection device as claimed in claim 1, characterized in that the closing position (P1) and the opening position (P2) are secured by a catch element (77) acting between the housing (7) and control sleeve (6) and by depressions (77A, 77B) in the housing (7) which act in a manner offset relative to one another by the control angle (α).

13. The injection device as claimed in claim 9, characterized in that the slide (2) is designed, over a first portion (2A) guided in the housing (7), as a hollow cylinder in which the tappet (4) is centrally mounted axially displaceably.

14. The injection device as claimed in claim 13, characterized in that the slide (2) has a U-shaped cross section in a second portion (2B) guided in the housing 10 (7), and a groove-shaped or slit like retention (21) for positioning the syringe collar (12) held in this retention (21) in such a way that the end face of the syringe plunger can be displaced in the injection direction by the tappet (4).

15. The injection device as claimed in claim 9, characterized in that the tappet (4) has, at it send pointing toward the handling portion (7A) of the housing (7), a guide portion (4A) which is guided in the 20 housing (7) and which has the same outside diameter as the first portion (2A) of the slide (2).

16. The injection device as claimed in claim 15, characterized in that a joint drive means for generating the two strokes (H1, H2) by the slide (2) and the tappet (4) is accommodated between the rear end face of the guide portion (4A) of the tappet (4) and the housing rear wall (74).

17. The injection device as claimed in claim 16, characterized in that the drive means is a helical spring (3) arranged coaxially to the longitudinal axis (F).

18. The injection device as claimed in claim 15, wherein a first stroke (H1) of a slide (2), in which the syringe (1) is held for introducing the injection needle (13) is provided, within the housing (7), between a locking position (A1) and an advanced position (V1), and characterized in that a second stroke (H2) of a tappet (4) in the operational axis (F) relative to the slide (2) for injecting the injection fluid is provided, within the housing (7), between a locking position (A2) and an advanced position (V2), and in that there is integrally formed on the rear side of the guide portion (4A) of the tappet (4) at least on securing pawl (41) which, in the opening and securing position (P2), is in releasable engagement with at least one control pawl (53, 54) of the trigger means, said control pawl being displaceable transversely to the longitudinal axis (F), and which holds the tappet (4) in its locking position (A1) counter to the pretension of the helical spring (3).

19. The injection device as claimed in claim 18, characterized in that the trigger means is guided outward through the housing (7) and there forms an actuating button (5) for releasing the securing pawl (41) and, consequently, the two strokes (H1, H2).

20. The injection device as claimed in claim 19, characterized in that the displacement of the actuating button (5) is possible only when the control sleeve (6) is in the closing and operating position (P1).

21. The injection device as claimed in claim 20, characterized in that the cylindrical control portion (6A) of the control sleeve (6) has an edge recess (6A1), through which a nose (5A) of the actuating button (5) can pass in the closing and operating position (P1).

22. The injection device as claimed in claim 15, characterized in that control elements are held in the guide portion (4A) of the tappet (4), said control elements cooperating with profiles which form at least one control cam are formed on the inner casing surface (MI) of the cylindrical control portion (6A) of the control sleeve (6) and which act as control cams (64, 66; 65, 67).

23. The injection device as claimed in claim 22, characterized in that in the control elements consist of at least one lifting bolt (42,43) which loads the control cam portions (64, 67; 65, 66; 68, 69) in such a way that, as a result of rotation of the control sleeve (6) from the closing and operating position (P1), after the execution of the two strokes (H1, H2), through the functional angle into the opening and securing position (P2), the torque applied at the same time is converted via the control cam portions (64, 67; 65, 66; 68, 69) into a linear restoring force counter to the tension force of the helical spring (3), with the result that the tappet (4) and the slide (2) execute a counterstroke (OH) in the housing (7) until in their locking positions (A1, A2), the securing pawls (41) of the tappet (4) come into engagement with the control pawls(53, 54) of the trigger means (5) again.

24. The injection device as claimed in claim 23, characterized in that two lifting bolts (42, 43) of different thickness spring-loaded in the direction of the casing surface (MI) are provided, which are guided by two control cams (64, 67 and 65, 66) arranged so as to be offset vertically in the inner casing surface (MI) in such a way that, in each axial position of the tappet (4), the conversion of the torque of the control sleeve (6) takes place via at least one of the lifting bolts (42, 43).

25. The injection device as claimed in claim 1, characterized in that the control sleeve (6), when in the closing and operating position (P1), allows a view of the syringe (1).

26. The injection device as claimed in claim 25, characterized in that the control sleeve (6) is made at least partially from transparent plastic.

27. The injection device as claimed in claim 1, characterized in that at least some of the essential structural operating parts (2, 4, 6, 7) are formed from plastic.

28. The injection device as claimed in claim 6, characterized in that the acceleration of the slide (2) into its advanced position (V1) during the first stroke (H1) is limited by a rotation damper (100) which is connected to the housing (7) via a rack (101).

29. The injection device as claimed in claim 23, characterized in that the housing (7) has an essentially cylindrical middle portion (7B) which has, over part of its circumference, a loading orifice (L7) for inserting and extracting the syringe (1), and in that there is provided opposite the loading orifice (L7) of the housing (7) an ejection means which, after injection has taken place, lifts the syringe (1) in the direction of the loading orifices (L6, L7) during the opening of the loading orifice (L7) as a result of the rotation of the control sleeve (6) into the opening and securing position (P2).

30. The injection device as claimed in claim 29, characterized in that the ejection means contains an ejection lever (200), one end of which is held pivotably on the slide (2) by means of a pin (201), in such a way that its other end can be moved in the direction of the syringe (1).

31. The injection device as claimed in claim 30, characterized in that, in order to control the movement of the ejection lever (200), the latter has a control boss which, at the end of the first stroke (H1), comes into engagement with a guide track (205) which rises in the direction of the operating axis (F) in a ramplike manner opposite to the injection direction, so that the lifting of the ejection lever (200) takes place during the rotation of the control sleeve (6) into the opening and securing position (P2).

32. The injection device as claimed in claim 31, characterized in that the control boss consists of two sliding bosses (202) which are arranged in a forklike manner on the ejection lever (200) and which are guided in a guide channel (203) narrowing in the stroke direction, until their ends pointing outward in a hooklike manner come into engagement with the lower end of the guide track (205).

33. The injection device as claimed in claim 1, characterized in that a signal means is provided, which is actuated at the end of the second stroke (H2) after injection has taken place.

34. The injection device as claimed in claim 33, characterized in that the signal means consists solely of mechanically acting structural elements.

35. The injection device as claimed in claim 33, characterized in that the signal means generates an acoustic signal.

36. The injection device as claimed in claim 34, characterized in that the signal means generates an acoustic signal and in that the signal is generated by means of a bell (306), the edge region of which is loaded by means of a striking pin (305) in order to generate the signal.

37. The injection device as claimed in claim 36, characterized in that the striking pin (305) is actuated, via a lever arrangement (302), by a tension rod (300) displaceable parallel to the operating axis (F) by the slide (2) and loaded by a spring (309).

38. The injection device as claimed in claim 37, characterized in that the striking pin (305) is secured by means of springs (304, 307) and is loaded in such a way that the bell (306) receives only a short pulse for generating the signal.

39. The injection device of claim 6, characterized in that the tappet (4') is coupled via a linear gear to a thrust rod (4"), which actuates the syringe plunger (14).

40. The injection device of claim 39, characterized in that the ratio of the gear is selected such that the second stroke (H2) of the tappet (4') is converted into a stroke in the same direction of the thrust rod (4"), which corresponds to the injection stroke of the syringe plunger (14).

41. The injection device of claim 40, characterized in that the thrust rod (4") is guided parallel to the tappet (4') by the slide (2').

42. The injection device of claim 41, characterized in that the front portion of the tappet (4'), at least two gear wheels (Z1, Z2) of different diameter are coaxially secured to one another, of which the first gear wheel (Z1) meshes with a first rack (S1) on the thrust rod (4"), and the second gear wheel (Z2) meshes with a second rack (S2) on the slide (2').

43. The injection device of claim 40, characterized in that the front portion of the tappet (4'), at least two gear wheels (Z1, Z2) of different diameter are coaxially secured to one another, of which the first gear wheel (Z1) meshes with a first rack (S1) on the thrust rod (4"), and the second gear wheel (Z2) meshes with a second rack (S2) on the slide (2') and in that the diameter of the two gear wheels (Z1, Z2) specifies the ratio of the gear (Z1, Z2; S1, S2).

44. The injection device of claim 43, characterized in that the front portion of the tappet (4') fits in forklike fashion over an arrangement of three gear wheels (Z2A, Z1, Z2B), of which the middle, first gear wheel (Z1) has the larger diameter, and the two outer, second gear wheels (Z2A, Z2B) mesh with two second racks (S2A, S2B).

45. The injection device of claim 42, characterized in that the first rack (S1) is an integral part of the thrust rod (4").

46. The injection device of claim 42, characterized in that the second rack or racks (S2; S2A, S2B) are an integral part of the slide (2').

47. The injection device of claim 39, characterized in that the longitudinal axis of the syringe (1) is located parallel to the longitudinal axis (F) of the housing (7).

48. The injection device of claim 41, characterized in that in the front portion of the tappet, a gear wheel is supported which meshes with a first rack on the thrust rod and with a second rack on the injection stroke is twice as long as the stroke of the tappet.

* * * * *